(12) United States Patent
Williams et al.

(10) Patent No.: US 10,959,671 B2
(45) Date of Patent: Mar. 30, 2021

(54) TECHNOLOGIES FOR MEASURING HYDRATION LEVEL OF A USER

(71) Applicant: Intel Corporation, Santa Clara, CA (US)

(72) Inventors: Bridget Williams, San Francisco, CA (US); Jonathan Lee, San Carlos, CA (US); Mark Ries Robinson, Albuquerque, NM (US); Elena Adelle Allen, Albuquerque, NM (US); Fahimeh Salehpour, Albuquerque, NM (US)

(73) Assignee: Intel Corporation, Santa Clara, CA (US)

( * ) Notice: Subject to any disclaimer, the term of this patent is extended or adjusted under 35 U.S.C. 154(b) by 196 days.

(21) Appl. No.: 15/859,395

(22) Filed: Dec. 30, 2017

(65) Prior Publication Data

US 2019/0038221 A1   Feb. 7, 2019

(51) Int. Cl.
*A61B 5/1455* (2006.01)
*A61B 5/00* (2006.01)
*A61B 5/11* (2006.01)
*A61B 5/145* (2006.01)

(52) U.S. Cl.
CPC .......... *A61B 5/4875* (2013.01); *A61B 5/0017* (2013.01); *A61B 5/1116* (2013.01); *A61B 5/14551* (2013.01); *A61B 5/6824* (2013.01); *A61B 5/0022* (2013.01); *A61B 5/14535* (2013.01); *A61B 5/14552* (2013.01); *A61B 5/6801* (2013.01); *A61B 5/742* (2013.01)

(58) Field of Classification Search
None
See application file for complete search history.

(56) References Cited

U.S. PATENT DOCUMENTS 6,819,950 B2   11/2004   Mills
2018/0317786 A1*  11/2018  Kulach .............. A61B 5/02438

* cited by examiner

*Primary Examiner* — Marjan Fardanesh
(74) *Attorney, Agent, or Firm* — Alliance IP, LLC

(57) ABSTRACT

Technologies for measuring a hydration level of a user includes a hydration measurement device having an arm position sensor and one or more reflectance sensors. The hydration measurement device generates sensor data indicative of a position of a user's arm using the arm position sensor. The hydration measurement device performs reflectance measurements with the reflectance sensor(s) at a first position that is determined based on the sensor data and a second position that is raised relative to the first position that is also based on the sensor data. The hydration measurement device determines a hematocrit of the user's blood based on the reflectance measurements and determines a hydration level of the user based on the determined hematocrit. Other embodiments are described and claimed.

25 Claims, 11 Drawing Sheets

TECHNOLOGIES FOR MEASURING HYDRATION LEVEL OF A USER

BACKGROUND

Wearable compute devices are increasingly equipped with various sensors to monitor the health of the user. Such wearable compute devices may come in many different form factors such as a smart bracelet, smart watch, a wearable monitor, or the like. Furthermore, these wearable compute devices are increasingly used during athletic endeavors. During these endeavors the user's hydration level fluctuates based upon many different factors including but not limited to the user's exertion, weather, and the user's hydration. Monitoring of the user's hydration is important because dehydration may lead to reduced performance and heat intolerance.

During certain circumstances, measuring a user's hydration while performing an athletic endeavor may have its challenges. For example, sweating, rehydration, and a requirement for a user to be stationary may lead to inaccurate measurements while the user is performing the athletic endeavor.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
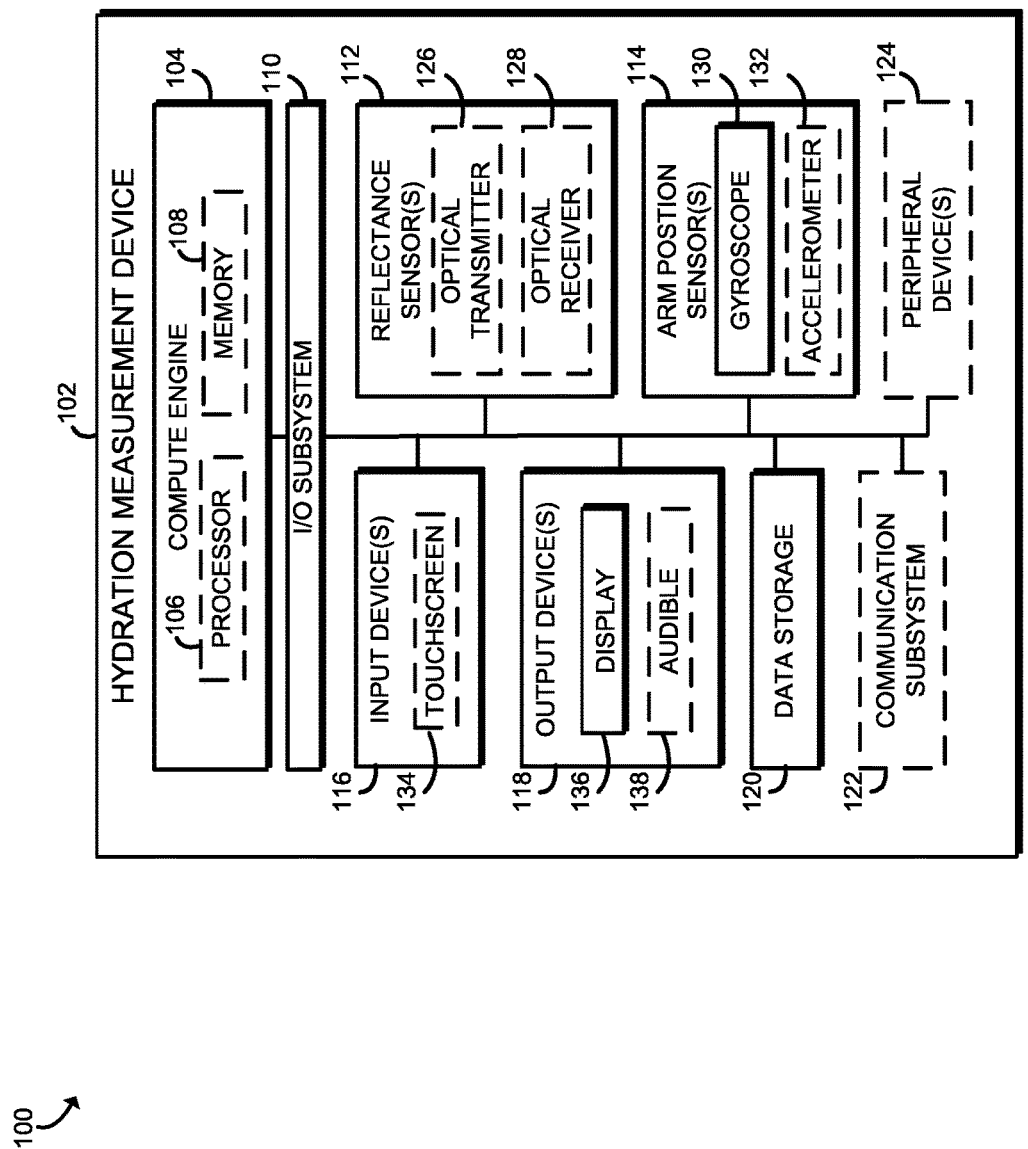
FIG. 1 is a simplified block diagram of at least one embodiment of a hydration measurement device for measuring a hydration level of a user.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a system 100 for measuring hydration includes a hydration measurement device 102 configured to determine the hydration level of a user while the user is wearing the hydration measurement device 102. To do so, the hydration measurement device 102 is configured to perform reflectance measurements indicative of blood and tissue analytes on a user's body part, such as a user's wrist. Such measurements are then processed by the hydration measurement device 102 to determine various attributes of the blood such as hemoglobin content and water content. This is achieved by leveraging the fact that the different substances have different absorbances based on the wavelength of the signal used to conduct the measurements. After extracting the various attributes of the blood from the reflectance measurements, the hydration measurement device 102 may examine the relationship between the various attributes to determine a hematocrit value of the blood. From the hematocrit value, the hydration measurement device 102 may determine a hydration level of the user.

As described in more detail below, in use, the hydration measurement device 102 may request the user to position his or her arm in two or more different positions to take reflectance measurements on the user's wrist in those different positions. Of course, in other embodiments, the hydration measurement device 102 may be worn on other body parts to perform similar measurements to determine the user's hydration level. Those different positions allow the hydration measurement device 102 to extract a blood signal from the reflectance measurements taken at the different positions. For example, one position may be a position in which a larger volume of blood would be flowing through the wrist, such as an arm placed by the user's side, and another position may be a position in which a smaller volume of blood would be flowing through the wrist, such as a raised arm over the shoulder or otherwise raised or elevated relative to the initial position. The reflectance measurements taken at the various positions may help eliminate the noise in the measurements by effectively isolating the blood signal through the combination of the measurements taken at these two positions as described in more detail below. For example, the hydration measurement device 102 may isolate or otherwise remove noise in the reflectance measurements that is associated with the tissue of the user's wrist. Alternatively, in some embodiments, the hydration measurement device 102 may take the reflectance measurements at various positions to help eliminate the noise in measurements by effectively isolating the tissue analyte signal. For example, the hydration measurement device 102 may isolate or otherwise remove noise in the reflectance measurements that is associated with the blood signal of the user's wrist to isolate the tissue analyte signal. Additionally, in some embodiments, the hydration measurement device 102 may isolate both the blood signal and tissue analyte signal to effectively determine the hydration of the user and combine the two measurements to more accurately determine the hydration of the user. As such, it should be appreciated that although the blood signal will be referenced below, the tissue analyte signal and/or a combination of the two may be contemplated as being measured by the hydration measurement device 102.

The hydration measurement device 102 may be embodied as any type of compute device capable of being worn or carried by a user and performing the functions described herein. For example, the hydration measurement device 102 may be embodied as a smart bracelet, a smartwatch, a fitness tracker, smart glasses, smart clothing or accessories, and/or another computing/communication device capable of being worn by the user. In other embodiments, the hydration measurement device 102 may be embodied as a smart phone, a smartphone, a tablet computer, a laptop computer, a notebook, a netbook, an Ultrabook™, a smart device, a personal digital assistant, a mobile Internet device, and/or any other computing/communication device capable of being carried by the user. Depending on the form factor, the hydration measurement device 102 may include a strap and/or other coupling mechanism to allow attachment to the user.

As shown in FIG. 1, the illustrative hydration measurement device 102 includes a compute engine 104, an input/output ("I/O") subsystem 110, one or more reflectance sensor(s) 112, one or more arm position sensor(s) 114, one or more input devices 116, one or more output devices 118, and a data storage device 120. In some embodiments, the hydration measurement device 102 may also include a communication subsystem 122 and peripheral devices 124. Of course, the hydration measurement device 102 may include other or additional components, such as those commonly found in a typical compute device, in other embodiments. Additionally, in some embodiments, one or more of the illustrative components may be incorporated in, or otherwise form a portion of, another component.

The compute engine 104 may be embodied as any controller, functional block, digital logic, or other component, device, circuitry, or collection thereof capable of performing the functions described herein. In some embodiments, the compute engine 104 may include a processor 106 and a memory 108. In such embodiments, the processor 106 may be embodied as any type of processor capable of performing the functions described herein. For example, the processor 106 may be embodied as a single or multi-core processor(s), digital signal processor, microcontroller, or other processor or processing/controlling circuit. Similarly, the memory 108 may be embodied as any type of volatile or non-volatile memory or data storage capable of performing the functions described herein. In operation, the memory 108 may store various data and software used during operation of the wearable compute device 102 such as operating systems, applications, programs, libraries, and drivers. The memory 108 is communicatively coupled to the processor 106 via the I/O subsystem 110, which may be embodied as circuitry and/or components to facilitate input/output operations with the processor 106, the memory 108, and other components of the wearable compute device 102. For example, the I/O subsystem 110 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 110 may form a portion of a system-on-a-chip (SoC) and be incorporated, along with the processor 106, the memory 108, and other components of the wearable compute device 102, on a single integrated circuit chip. In some embodiments, the memory 108, or portions of the memory 108 may be incorporated into the processor 106.

The reflectance sensor(s) 112 may be embodied as any one or more sensors capable of performing reflectance measurements. Additionally, the reflectance sensor(s) 112 may be embodied as any one or more sensors capable of generating or producing sensor data indicative of one or more reflectance measurement values of a user's blood. For example, in some embodiments, the reflectance sensor(s) 112 may include an optical transmitter 126 and an optical receiver 128 configured to generate reflectance measurement values of the user's blood based on optical signals transmitted through the skin of the user. In other embodiments, additional or other sensors may be included in the hydration measurement device 102 to generate sensor data indicative of the one or more reflectance measurement values of a user's blood.

The arm position sensor(s) 114 may be embodied as any one or more sensors capable of generating or producing sensor data indicative of a present position of an arm of the user. The sensor data may be embodied as any type of data capable of detecting the position of the arm relative to the user's body. For example, in some embodiments, the sensor data produced by the arm position sensor(s) 114 may be indicative of an angle of the arm in relation to the user's body. In such scenarios, the angle may be set to 0 degrees when the user's arm is placed by the user's sides and the angle may be set to 180 degrees when the user's arm is placed above the user's shoulders. In the illustrative embodiment, the arm position sensor(s) 114 includes one or more gyroscopes 130. In some embodiments, the arm position sensor(s) may include one or more accelerometers 132. In other embodiments, additional or other sensors may be included in the hydration measurement device 102 to generate sensor data indicative of the position of the user's arm.

The input device(s) 116 may be embodied as any one or more devices capable of receiving an interaction from a user of the hydration measurement device 102 and providing an input to the hydration measurement device 102 based on such interaction. In some embodiments, the input device(s) 116 may include a touchscreen 134, which may receive input from the user based on a tactile interaction. Of course, the input device(s) 116 may include additional or other types of input devices such as a physical or virtual keyboard, buttons, switches, microphones, a mouse, and so forth.

The output device(s) 118 may include, or be embodied as, any type of output device capable of providing information to the user of the hydration measurement device 102. In the illustrative embodiment, the output device(s) 118 include a display 136. In some embodiments, the output device(s) 118 may include an audible device 138. The output device(s) 118 may include additional or other components in other embodiments. The display 136 may be embodied as any type of display capable of displaying information to the user of the hydration measurement device 102. For example, the display 136 may be embodied as a liquid crystal display (LCD), a light emitting diode (LED) display, an organic light emitting diode (OLED), a cathode ray tube (CRT) display, a plasma display, and/or other display device. Additionally, in some embodiments, the touchscreen 134 may form a portion of the display 136. The audible 138 may be embodied as any type of audio generation device, such as a speaker or annunciator, capable of producing sound.

The data storage device 120 may be embodied as any type of device or devices configured for short-term or long-term storage of data such as, for example, memory devices and circuits, memory cards, hard disk drives, solid-state drives, non-volatile flash memory, or other data storage devices.

In some embodiments, the hydration measurement device 102 may also include a communication subsystem 122. The communication subsystem 122 may be embodied as any type of communication circuit, device, or collection thereof, capable of enabling communications between the hydration measurement device 102 and other remote devices such as other hydration measurement devices 102. To do so, the communication subsystem 122 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

In some embodiments, the hydration measurement device 102 may also include one or more peripheral device(s) 124. The peripheral device(s) 124 may include any number of additional peripheral or interface devices, such as other input/output devices, storage devices, and so forth. The particular devices included in the peripheral device(s) 124 may depend on, for example, the type and/or intended use of the hydration measurement device 102.

Figure 2:
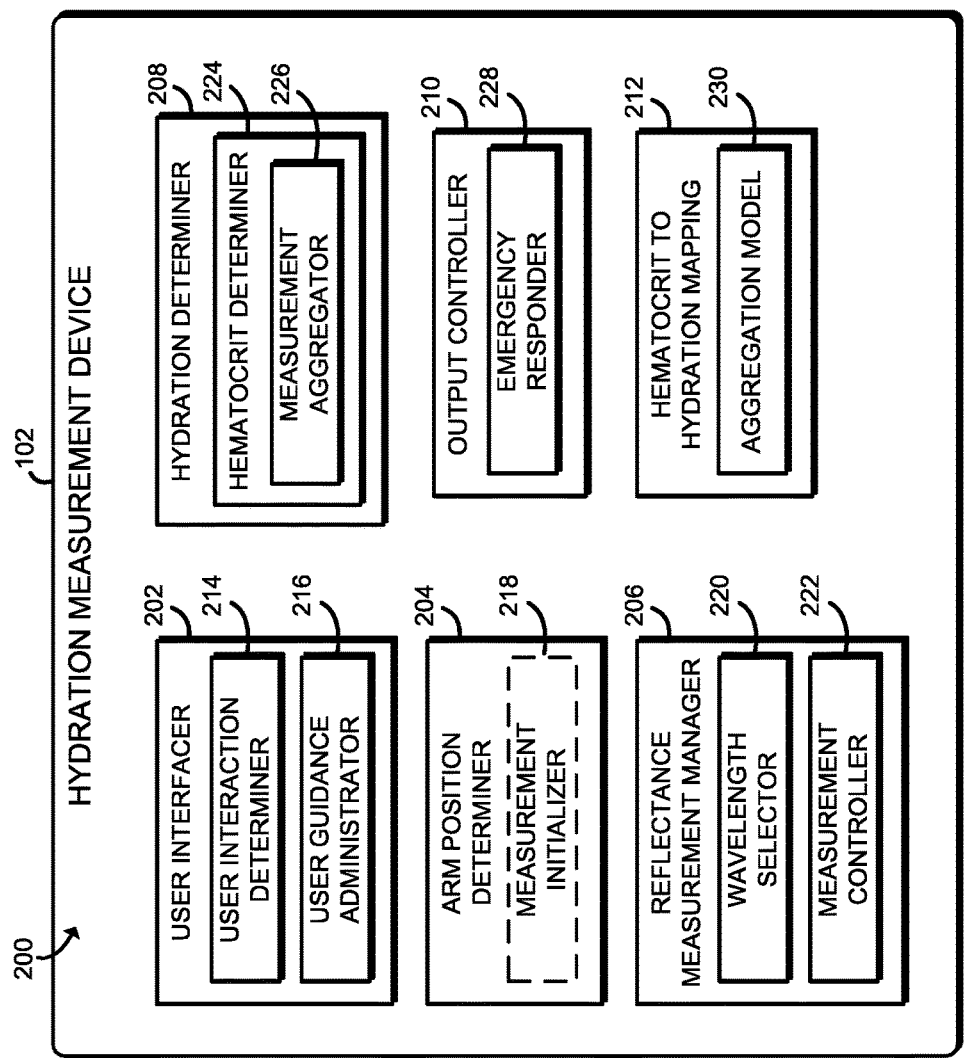
FIG. 2 is a simplified block diagram of at least one embodiment of an environment that may be established by the hydration measurement device of FIG. 1.

Referring now to FIG. 2, in the illustrative embodiment, the hydration measurement device 102 may establish an environment 200 during operation. The illustrative environment 200 includes a user interfacer 202, an arm position determiner 204, a reflectance measurement manager 206, a hydration determiner 208, an output controller 210, and a hematocrit-to-hydration mapping 212. Each of the components, logic, and other modules of the environment 200 may be embodied as hardware, firmware, software, or a combination thereof. As such, in some embodiments, one or more of the components of the environment 200 may be embodied as circuitry or collection of electrical devices (e.g., user interfacer circuitry 202, arm position determiner circuitry 204, etc.). It should be appreciated that, in some embodiments, one or more of the user interfacer 202, the arm position determiner 204, the reflectance measurement manager 206, the hydration determiner 208, the output controller 210, and/or the hematocrit-to-hydration mapping 212 may form a portion of one or more of the compute engine 104, processor 106, memory 108, reflectance sensor(s) 112, arm position sensor(s) 114, and/or other components of the hydration measurement device 102. Additionally, in some embodiments, one or more of the illustrative components may form a portion of another component and/or one or more of the illustrative components may be independent of one another. Further, in some embodiments, one or more of the components of the environment 200 may be embodied as virtualized hardware components or emulated architecture, which may be established and maintained by the processor 106 or other components of the hydration measurement device 102.

The user interfacer 202, which may be embodied as hardware, firmware, software, virtualized hardware, emulated architecture, and/or a combination thereof as described above, is configured to control user interaction with the hydration measurement device 102 by facilitating user movement. As described above, the hydration measurement device 102 may require reflectance measurements taken at multiple different positions (e.g., at two different positions). Under those circumstances, in some embodiments, the hydration measurement device 102 may communicate with the user to achieve that outcome. In the illustrative embodiment, the user interfacer 202 includes a user interaction determiner 214 and a user guidance administrator 216. The user interaction determiner 214 is configured to detect user interaction with the hydration measurement device 102. For example, the user interaction determiner 214 may detect a selection by the user to measure the hydration level. The user interaction determiner 214 may also detect a gesture performed by the user to initiate the hydration measurement process.

After the user interaction determiner 214 detects the input from the user to measure his or her hydration level, the user guidance administrator 216 provides instructions through the output device(s) 118 to instruct the user to position his or her arm in multiple positions. For example, the user guidance administrator 216 may instruct the user to lower his or her arm by the user's side and subsequently instruct the user to raise his or her arm over the user's shoulders (or to another raised position relative to the initially measured position). Alternatively, the user guidance administrator 216 may instruct the user to raise his or her arm over the user's shoulders and then lower the user's arm by the user's side. In other embodiments, the user guidance administrator 216 may instruct the user to position his or her arm in multiple different positions. The instructions may be presented to the user through the display 136, the speaker 138, and/or a combination of the two. In addition, the instructions may be at least one of a visual, audible, or tactile instruction to the user.

The arm position determiner 204, which may be embodied as hardware, firmware, software, virtualized hardware, emulated architecture, and/or a combination thereof as described above, is configured to identify a present position of the user's arm. The arm position determiner 204 may also generate sensor data indicative of the position of the user's arm. During the circumstances in which the user interfacer 202 is providing instructions to the user, the arm position determiner 204 may detect whether the user's arm is positioned in an appropriate or expected position (e.g., in either a lowered or raised position, relative to the "lowered" position) to thereby verify that the user's arm is actually in the correct requested position. For example, the arm position determiner 204 may identify when the user's arm is at 0 degrees or 180 degrees relative to the user's body as described above. Alternatively in other embodiments, the arm position determiner 204 may identify when the user's arm is at other angles relative to the user's body. When the user's arm is in the correct position as determined by the arm position determiner 204, the hydration measurement device 102 may proceed with performing the reflectance measurements as described below.

In some embodiments, the arm position determiner 204 may include a measurement initializer 218 configured to determine whether or not to perform reflectance measurements. For instance, the user may select to automatically measure the hydration level of the user. Under those conditions, the measurement initializer 218 may monitor the position of the user's arm and when the user's arm reaches positions indicative of a reference position (e.g., a "raised" or "lowered" position, the measurement initializer 218 may instruct the hydration measurement device 102 to perform the reflectance measurements at that position. The arm position determiner 204 may store the collected data to be accessed later for a determination of the hydration level of the user.

The reflectance measurement manager 206, which may be embodied as hardware, firmware, software, virtualized hardware, emulated architecture, and/or a combination thereof that is configured to control the reflectance sensor(s) 112 to perform reflectance measurements to determine reflectance measurement values of the user's blood. In the illustrative embodiment, the reflectance measurement manager 206 includes a wavelength selector 220 and a measurement controller 222. As described above, different wavelengths are used to perform the reflectance measurements to extract the various attributes of the user's blood. For example, a wavelength or a set of wavelengths may be selected to perform a reflectance measurement to generate a hemoglobin signal and another wavelength or set of wavelengths may be selected to perform a reflectance measurement to generate a water signal. Additionally or alternatively, there may be other attributes of the user's blood that are used for determination of the hydration level of the user. The wavelength selector 220 is configured to select a wavelength to be used for a reflectance measurement when the arm position determiner 204 identifies that the user's arm is in a positioned to be measured (e.g., a "lowered" or "raised position, relative to the "lowered" position). Furthermore, the wavelength selector 220 may select several wavelengths to be used for several reflectance measurements at the lowered or raised position. In some embodiments, the wavelengths may be selected from a range of 800 nm to 1600 nm. Furthermore, in some embodiments, wavelengths may be selected from at least one of 808 nm, 830 nm, 870 nm, 910 nm, 940 nm, 970 nm, 1050 nm, 1070 nm, 1200 nm, 1300 nm, 1450 nm, and/or 1550 nm. The measurement controller 222 is configured to perform the reflectance measurements after the wavelength(s) are selected. The reflectance measurement manager 206 may store the collected data to be accessed later for a determination of the hydration level of the user.

The hydration determiner 208, which may be embodied as hardware, firmware, software, virtualized hardware, emulated architecture, and/or a combination thereof that is configured to determine the hydration level of the user. In the illustrative embodiment, the hydration determiner 208 includes a hematocrit determiner 224 and the hematocrit determiner 224 includes a measurement aggregator 226. The hematocrit determiner 224 is configured to determine the hematocrit value of the user's blood from the reflectance measurements. To do so, the measurement aggregator 226 is configured to aggregate the collected data from the arm position determiner 204 and the reflectance measurement manager 206. This is done by initially separating the reflectance measurements taken at each different wavelength and normalizing the reflectance measurements taken at each wavelength. For example, the reflectance measurement manager 206 selects one wavelength to perform a reflectance measurement at both a raised and a lowered arm position. After performing the two reflectance measurements, the measurement aggregator 226 normalizes the two reflectance measurements to receive a normalized value. For example, the measurement aggregator 226 may take the reflectance measurement value of the user's blood associated with a lower arm position and normalize that with the reflectance measurement value of the user's blood associated with an arm position that is raised or elevated relative to the lowered position. Subsequently, the measurement aggregator 226 performs this normalization procedure on the reflectance measurements taken at a different wavelength. Afterwards, the measurement aggregator 226 takes these two normalized values to determine the hematocrit value of the user's blood. From the hematocrit value, the hydration determiner 208 may determine the hydration level of the user.

The output controller 210, which may be embodied as hardware, firmware, software, virtualized hardware, emulated architecture, and/or a combination thereof that is configured to analyze the determined hydration level and perform a response based on the determined hydration level. The output controller 210 may communicate the hydration level of the user to the user through the output device(s) 118. In the illustrative embodiment, the output controller 210 includes an emergency responder 228. The emergency responder 228 is configured to alert the user of a critical hydration level if the user's hydration level is determined to be at a dangerous level. For example, the user may be severely dehydrated or severely overhydrated. Further to alerting the user, the emergency responder 228 may also alert a remote compute device to alert emergency personnel should the user need immediate assistance.

The hematocrit-to-hydration mapping 212, which may be embodied as hardware, firmware, software, virtualized hardware, emulated architecture, and/or a combination thereof that is configured to map the hematocrit values to a hydration level. For example, the determined hematocrit value may indicate that the user is hydrated. In the illustrative embodiment, the hematocrit-to-hydration mapping 212 includes an aggregation model 230 that is configured to determine the hydration level based on aggregated values.

Figure 3:
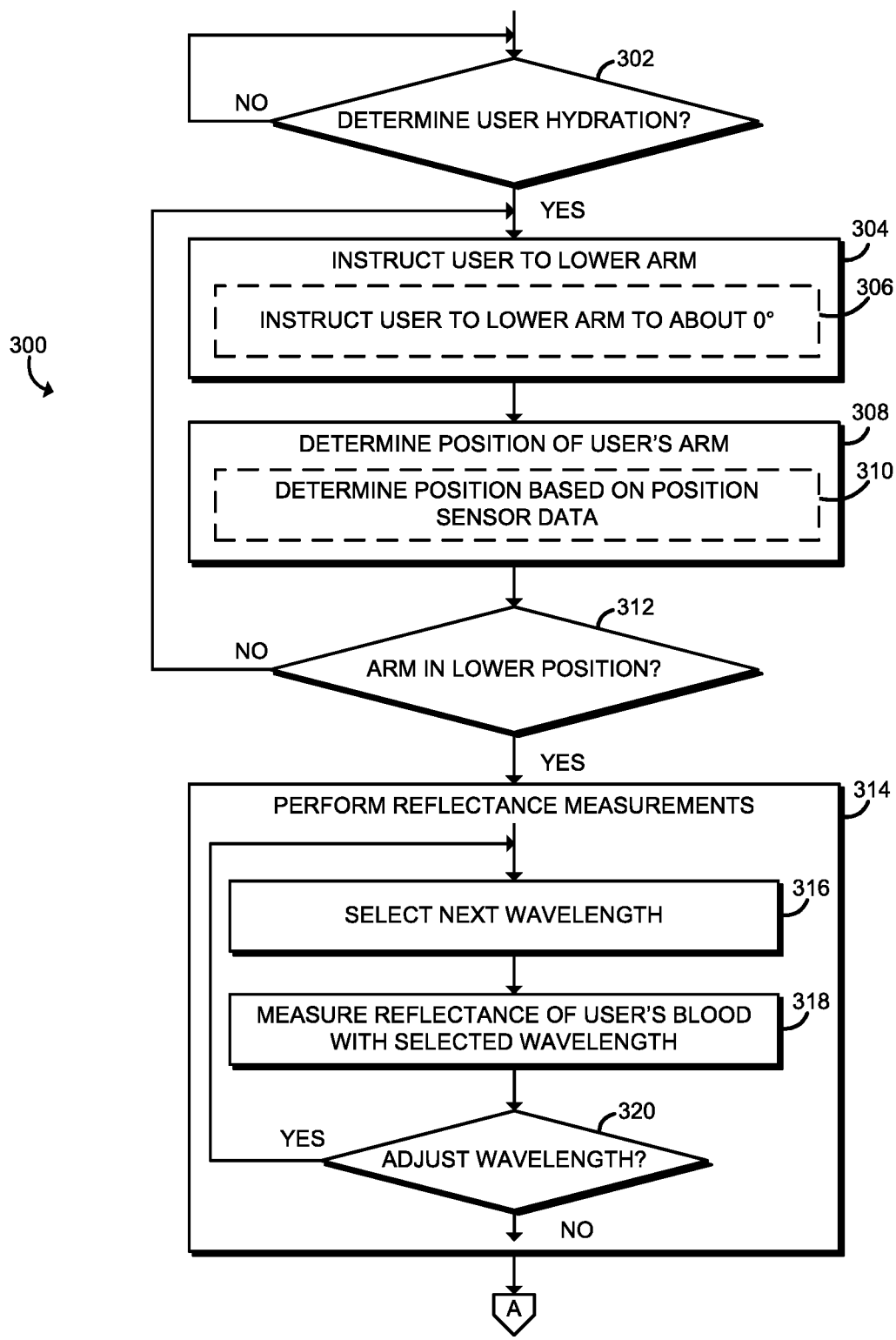
FIGS. 3-5 are a simplified flow diagram of at least one embodiment of a method for measuring a hydration level of a user that may be executed by the hydration measurement device of FIGS. 1 and 2.
Figure 4:
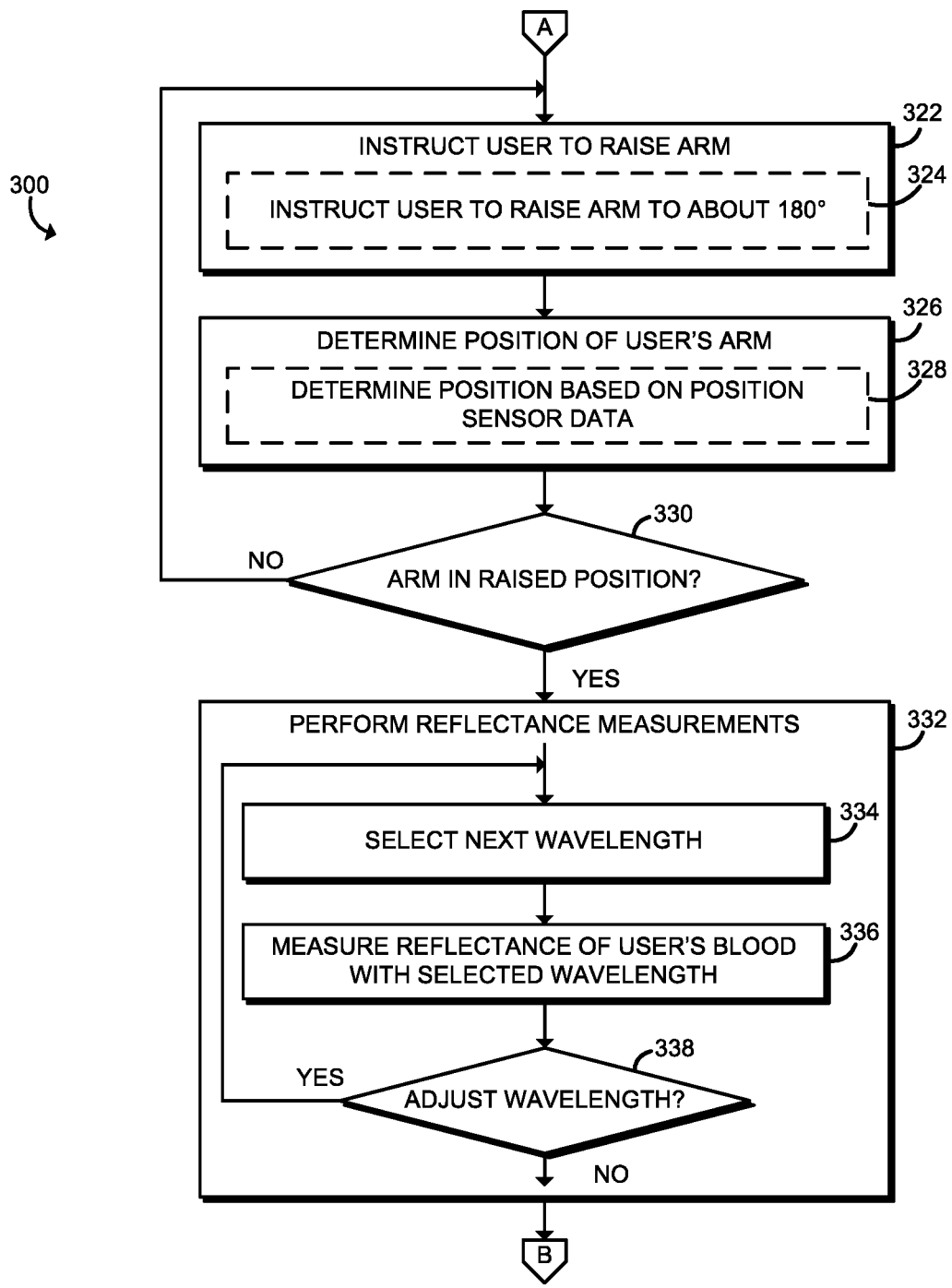
Figure 5:
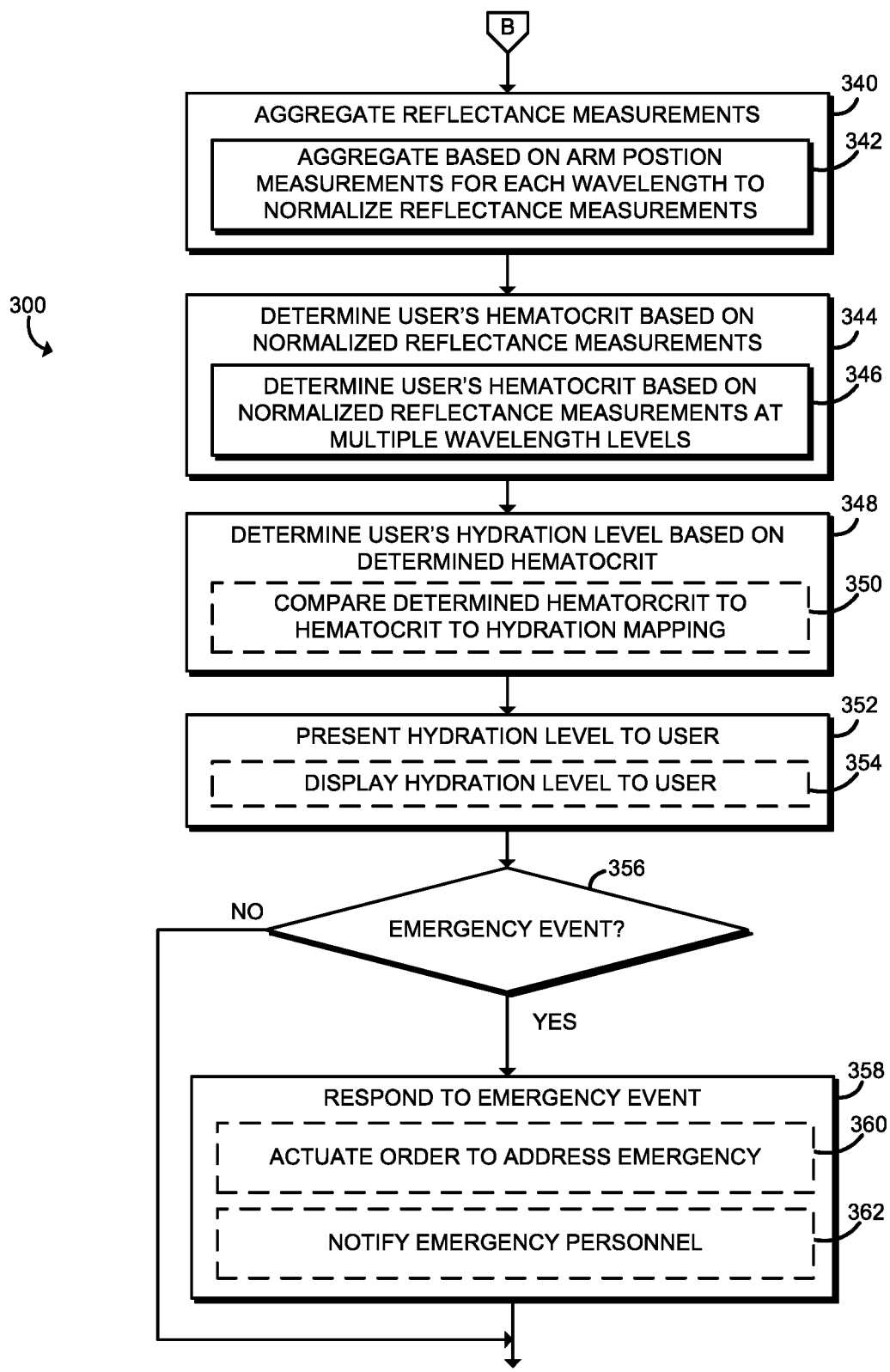

Referring now to FIGS. 3-5, in use, the hydration measurement device 102 may execute a method 300 for measuring a hydration level of a user of the hydration measurement device 102. The method 300 begins with block 302 in which the hydration measurement device 102 determines whether the user wants to determine his or her hydration level. To do so, in some embodiments, the hydration measurement device 102 may wait to receive an input from the user as described above. If it is determined that the user hydration is to be determined, the method 300 advances to block 304. However, if it is determined that user hydration is not to be determined, the method 300 loops back to the start of block 302.

In block 304, the hydration measurement device 102 instructs the user to position the user's arm in an initial "lower" position. For example, in block 306, the hydration measurement device 102 may instruct the user to lower his or her arm to about 0 degrees relative to the user's body (e.g., to instruct the user to place the user's arm by the user's side at approximately 0 degrees). It should be appreciated, however, that the "lower" position may be embodied as any position that is lower (e.g., has a smaller angle relative to the user's body) than the "raised" position and may have an angle relative to the user's body that is greater than 0 degrees in some embodiments. The hydration measurement device 102 may provide a visual, audible, or tactile instruction to the user.

In block 308, the hydration measurement device 102 determines the position of the user's arm. In particular, the hydration measurement device 102 may determine the position of the user's arm to which the hydration measurement device 102 and/or the reflectance sensors 112 are attached. To do so, in some embodiments, in block 310, the hydration measurement device 102 may determine the position of the user's arm based on position sensor data from the arm position sensor(s) 114.

In block 312, the hydration measurement device 102 determines whether the arm is in the "lowered" position based on the analysis performed in block 308. If it is determined that the arm is not in a lowered position, the method 300 loops back to block 304 to attempt the process again. If it is determined that the arm is in a lowered position, the method 300 advances to block 314.

In block 314, the hydration measurement device 102 performs reflectance measurements. In order to perform the reflectance measurements, the hydration measurement device selects a next wavelength to be used for the reflectance measurements in block 316. Then the hydration measurement device 102 measures the reflectance of the user's blood with the selected wavelength in block 318. After performing the measurement, the hydration measurement device 102 determines in block 320 whether to adjust the wavelength based on previous measurements taken. For instance, if the hydration measurement device 102 already has a sufficient amount of reflectance measurements at various wavelengths, the method 300 advances to block 322 of FIG. 4, described below. However, if it is determined not enough reflectance measurements have been taken at different wavelengths, the method 300 loops back to block 316 to select another wavelength.

In block 322, shown in FIG. 4, the hydration measurement device 102 instructs the user to position the user's arm in a second "raised" position. For example, in block 324, the hydration measurement device 102 may instruct the user to raise his or her arm to about 180 degrees relative to the user's body (e.g., to instruct the user to position the user's arm above the user's shoulders at approximately 180 degrees). It should be appreciated, however, that the "raised" position may be embodied as any position that is raised or elevated (e.g., has a larger angle relative to the user's body) relative to the "lowered" position and may have an angle relative to the user's body that is less than 180 degrees in some embodiments. Again, the hydration measurement device 102 may provide a visual, audible, or tactile instruction to the user.

In block 326, the hydration measurement device 102 determines the position of the user's arm similarly to how the position of the arm is determined in block 308. Additionally, in some embodiments, in block 328, the hydration measurement device 102 may determine the position of the user's arm based on position sensor data from the arm position sensor(s) 114.

In block 330, the hydration measurement device 102 determines whether the arm is in the "raised" position based on the analysis performed in block 326. If it is determined that the arm is not in the raised position, the method loops back to block 322 to attempt the process again. After several attempts, the method 300 may restart back at block 304. If it is determined that the arm is in a raised position, the method 300 advances to block 332.

In block 332, the hydration measurement device 102 performs reflectance measurements similarly to block 314 of FIG. 3, described above. Block 334, block 336, and block 338 correspond to block 316, block 318, and block 320 of FIG. 3 and thus the descriptions of blocks 316, 318, 320 are applicable to the corresponding blocks 334, 336, 338. Subsequent to a determination that no further reflectance measurements are required, the method 300 advances to block 340 of FIG. 5, described below.

In block 340, shown in FIG. 5, the hydration measurement device 102 aggregates the reflectance measurements taken at the two different arm positions. To do so, in block 342 the hydration measurement device 102 aggregates the reflectance measurements taken at each position for each separate wavelength to normalize the reflectance measurements as described above.

In block 344, the hydration measurement device 102 determines the user's hematocrit based on normalized reflectance measurements calculated in block 342. In addition to using normalized reflectance measurements, in block 346, the hydration measurement device 102 determines the user's hematocrit based on normalized reflectance measurements at multiple wavelength levels as described above.

In block 348, the hydration measurement device 102 determines the user's hydration level based on the determined hematocrit. To do so, in some embodiments, in block 350, the hydration measurement device 102 compares the determined hematocrit to a hematocrit-to-hydration mapping. For example, the hydration measurement device 102 may match a hematocrit value to the hematocrit-to-hydration mapping in order to identify a hydration level.

After the hydration measurement device 102 determines the user's hydration level, the hydration measurement device 102 presents the hydration level to the user in block 352. To do so, in some embodiments, in block 354, the hydration measurement device 102 displays the hydration level to the user.

In block 356, the hydration measurement device 102 analyzes the determined hydration level from block 348 to determine whether there is an emergency event. For example, if the user is severely dehydrated it may be important that the user is at least notified and given assistance to recuperate. If it is determined there is no emergency event, the method 300 is completed. If there is an emergency event, the method 300 advances to block 358.

In block 358, the hydration measurement device 102 responds to the emergency event identified in block 356. To do so, in some embodiments, in block 360, the hydration measurement device 102 may actuate an order to address the emergency. For example, the hydration measurement device 102 may instruct the user not to exert himself or herself any further and to drink more liquids, such as water, in the event that the emergency event is severe user dehydration. Additionally or alternatively, in some embodiments, in block 362 the hydration measurement device 102 may notify emergency personnel of the emergency event. The emergency personnel may be authorities or other personnel that may assist the user to recuperate and get medical attention if required. After responding to the emergency event, the method 300 is completed.

Although the hydration measurement device 102 instructs the user to position the user's arm in the "raised" position followed by the "lowered" position, it should be appreciated that the hydration measurement device 102 may instruct the user to position the user's arm in the "lowered" position first, followed by the "raised" position. Additionally, as discussed above, the hydration measurement device 102 may instruct the user to position the user's arm in an additional number of positions in other embodiments.

Figure 6:
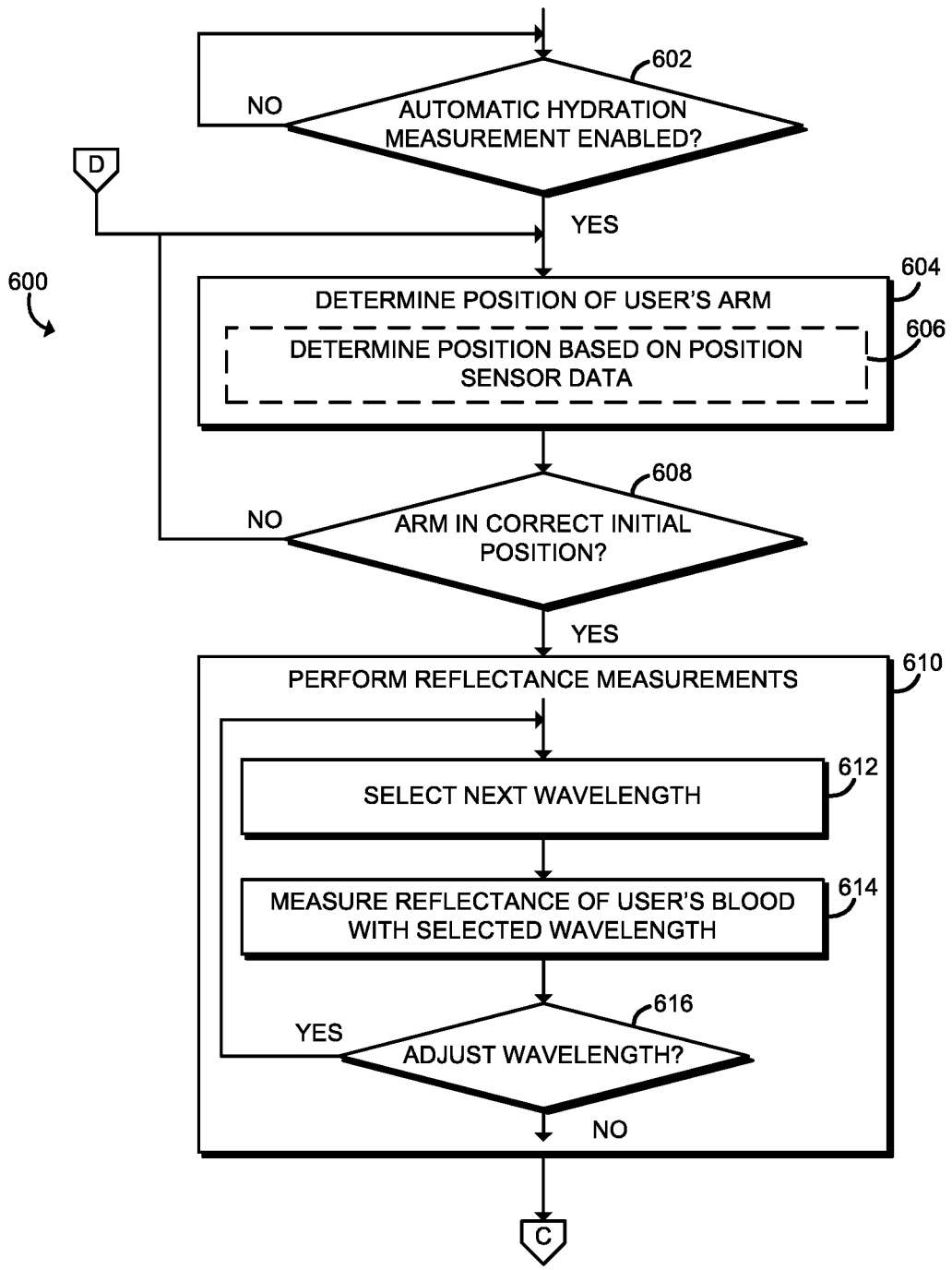
FIGS. 6-8 are a simplified flow diagram of another embodiment of a method for measuring a hydration level of a user that may be executed by the hydration measurement device of FIGS. 1 and 2.
Figure 7:
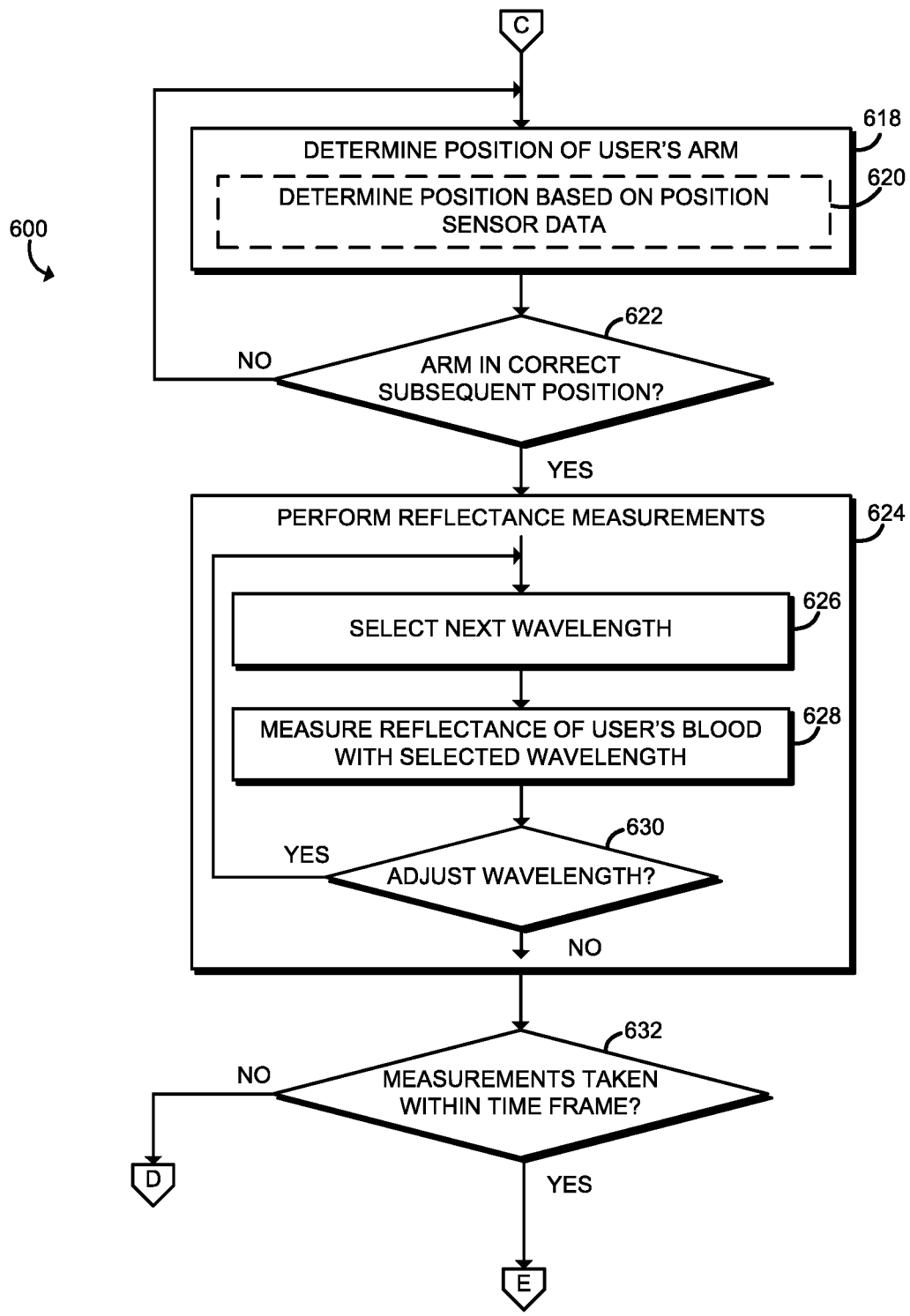
Figure 8:
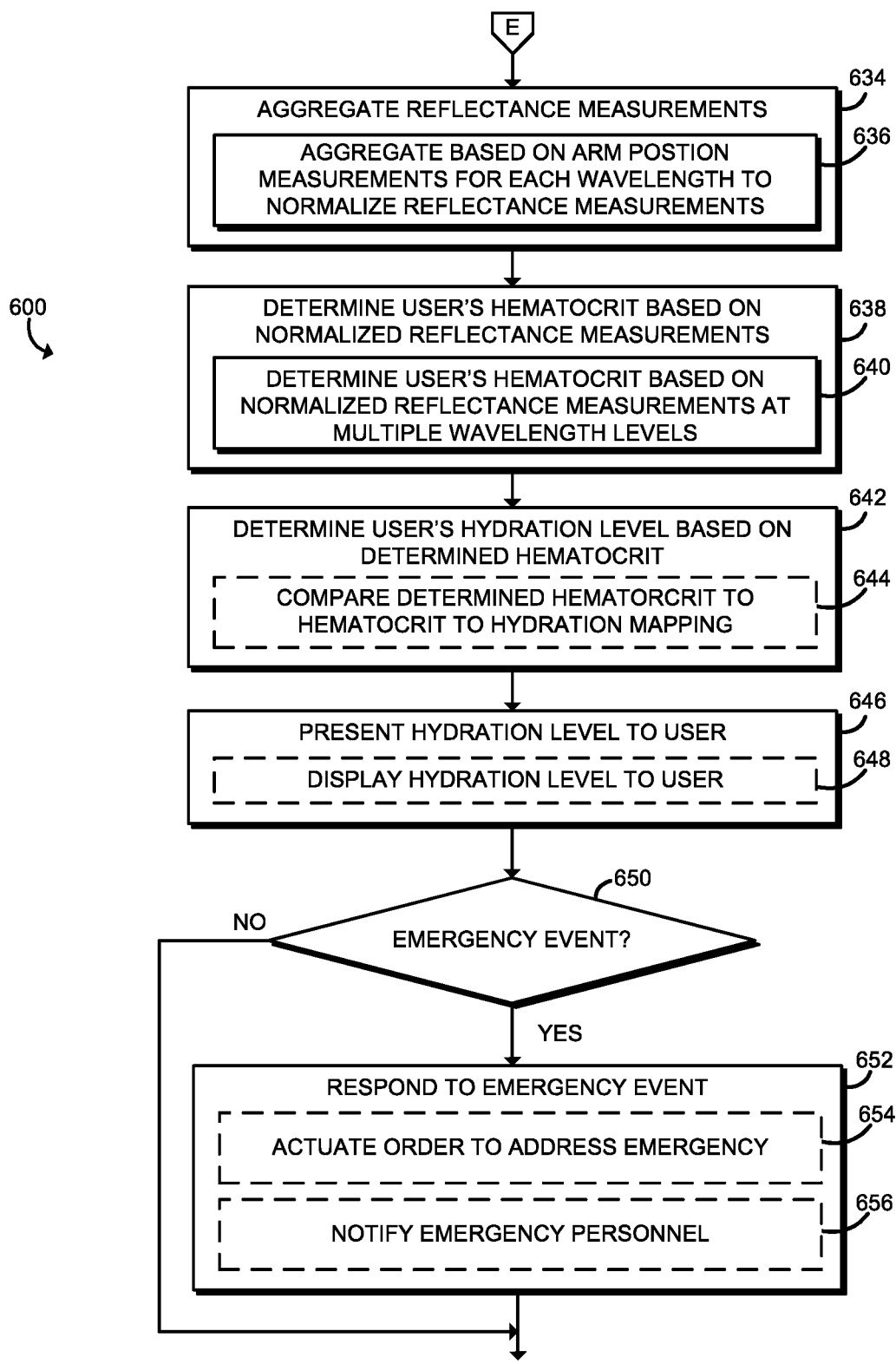

Referring now to FIGS. 6-8, in use, the hydration measurement device 102 may execute a method 600 for automatically measuring a hydration level of a user of the hydration measurement device 102 in some embodiments. The method 600 begins with block 602 in which the hydration measurement device 102 determines whether automatic hydration measurement is enabled. That is, the hydration measurement device 102 determines whether the user has selected to enable periodic, continuous, or constant hydration detection. If it is determined that automatic hydration measurement has not been enabled, the method 600 loops back to the start of block 602. If it is determined that the automatic hydration measurement has been enabled, the method 600 advances to block 604.

In block 604, the hydration measurement device 102 determines the present position of the user's arm. In particular, the hydration measurement device 102 may determine the position of the user's arm to which the hydration measurement device 102 and/or the reflectance sensors 112 are attached. To do so, in some embodiments, in block 606, the hydration measurement device 102 may determine the position of the user's arm based on position sensor data from the arm position sensor(s) 114.

In block 608, the hydration measurement device 102 determines whether the position of the arm is in a correct initial position based on the analysis performed in block 604. For example, the correct initial position may be either a referenced "lowered" position (i.e., 0 degrees) or a reference "raised" position (i.e., 180 degrees), relative to the referenced lowered position, as described above. If it is determined that the user's arm is not in the correct initial position, the method 600 loops back to block 604. However, if it is determined that the arm is in the correct initial position, the method 600 advances to block 610.

In block 610, the hydration measurement device 102 performs reflectance measurements similarly to block 314 of FIG. 3. Block 612, block 614, and block 616 correspond to block 316, block 318, and block 320 of FIG. 3 and thus the descriptions of blocks 316, 318, 320 are applicable to the corresponding blocks 612, 614, 616. Subsequent to a determination that no further reflectance measurements are required, the method 600 advances to block 618 of FIG. 7, described below.

In block 618, shown in FIG. 7, the hydration measurement device 102 determines the position of the user's arm. To do so, in some embodiments, in block 620, the hydration measurement device 102 may determine the position of the user's arm based on position sensor data from the arm position sensor(s) 114.

In block 622, the hydration measurement device 102 determines whether the position of the arm is in a correct subsequent position based on the analysis performed in block 618. For example, the correct subsequent position may be either a "lowered" position (i.e., 0 degrees), relative to the first or initial position, or a "raised" position (i.e., 180 degrees), relative to the first or initial position, as described above. Furthermore, the subsequent position is different from the correct initial position. That is, if the initial position was a "lowered" position, the subsequent position is a "raised" position, and vice versa. If it is determined that the arm is not in the correct subsequent position, the method 600 loops back to block 618. If it is determined that the arm is in the correct subsequent position, the method 600 advances to block 624.

In block 624, the hydration measurement device 102 performs reflectance measurements similarly to block 314 of FIG. 3. Block 626, block 628, and block 630 correspond to block 316, block 318, and block 320 of FIG. 3 and thus the descriptions of blocks 316, 318, 320 are applicable to the corresponding blocks 626, 628, 630. Subsequent to a determination that no further reflectance measurements are required, the method 600 advances to block 632.

In block 632, the hydration measurement device 102 determines whether the measurements have been taken within a time frame. Since the hydration measurement device 102 does not instruct the user to raise and/or lower his or her arm, then the hydration measurement device 102 must detect the position of the user's arm at each measurement position (e.g., at both a "raised" position and a "lowered" position) within a particular time frame, because if too long of a time frame elapses, the measurements may not correlate to the user's current hydration level. Thus, the time frame may be embodied as any time value that maintains the integrity of the reflectance measurements for determining a user's hydration level. If it is determined that the measurements were not taken within the time frame, such as after an hour, the method 600 loops back to the start of block 604. If it is determined that the measurements were taken within the time frame, such as within a few minutes, the method 600 advances to block 634 of FIG. 8.

In block 634, shown in FIG. 8, the hydration measurement device 102 aggregates the reflectance measurements taken at the two different arm positions. To do so, in block 636 the hydration measurement device 102 aggregates the reflectance measurements taken at each position for each separate wavelength to normalize the reflectance measurements as described above.

In block 638, the hydration measurement device 102 determines the user's hematocrit based on normalized reflectance measurements calculated in block 636. In addition to using normalized reflectance measurements, in block 640, the hydration measurement device 102 determines the user's hematocrit based on normalized reflectance measurements at multiple wavelength levels as described above.

In block 642, the hydration measurement device 102 determines the user's hydration level based on the determined hematocrit. To do so, in some embodiments, in block 644, the hydration measurement device 102 compares the determined hematocrit to a hematocrit-to-hydration mapping. For example, the hydration measurement device 102 may match a hematocrit value to the hematocrit-to-hydration mapping in order to identify a hydration level.

After the hydration measurement device 102 determines the user's hydration level, the hydration measurement device 102 presents the hydration level to the user in block 646. To do so, in some embodiments, in block 648, the hydration measurement device 102 displays the hydration level to the user.

In block 650, the hydration measurement device 102 analyzes the determined hydration level from block 642 to determine whether there is an emergency event. For example, if the user is severely dehydrated it may be important that the user is at least notified and given assistance to recuperate. If it is determined there is no emergency event, the method 600 is completed. If there is an emergency event, the method 600 advances to block 652.

In block 652, the hydration measurement device 102 responds to the emergency event identified in block 650. To do so, in some embodiments, in block 654, the hydration measurement device 102 may actuate an order to address the emergency. For example, the hydration measurement device 102 may instruct the user not to exert himself or herself any further and to drink more liquids, such as water, in the event that the emergency event is severe user dehydration. Additionally or alternatively, in some embodiments, in block 656 the hydration measurement device 102 may notify emergency personnel of the emergency event. The emergency personnel may be authorities or other personnel that may assist the user to recuperate and get medical attention if required. After responding to the emergency event, the method 600 is completed.

Figure 9:
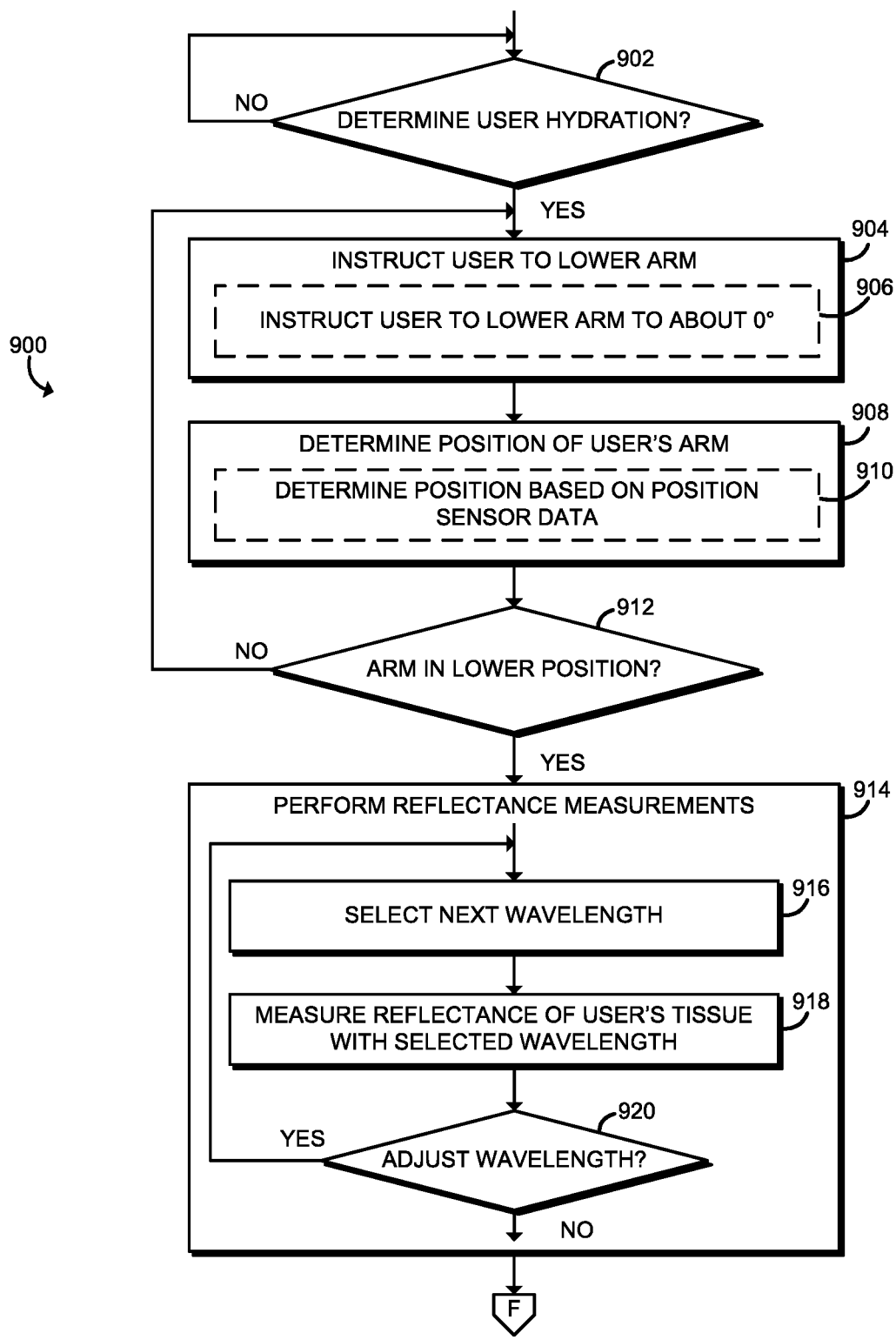
FIGS. 9-11 are a simplified flow diagram of another embodiment of a method for measuring a hydration level of a user that may be executed by the hydration measurement device of FIGS. 1 and 2.
Figure 10:
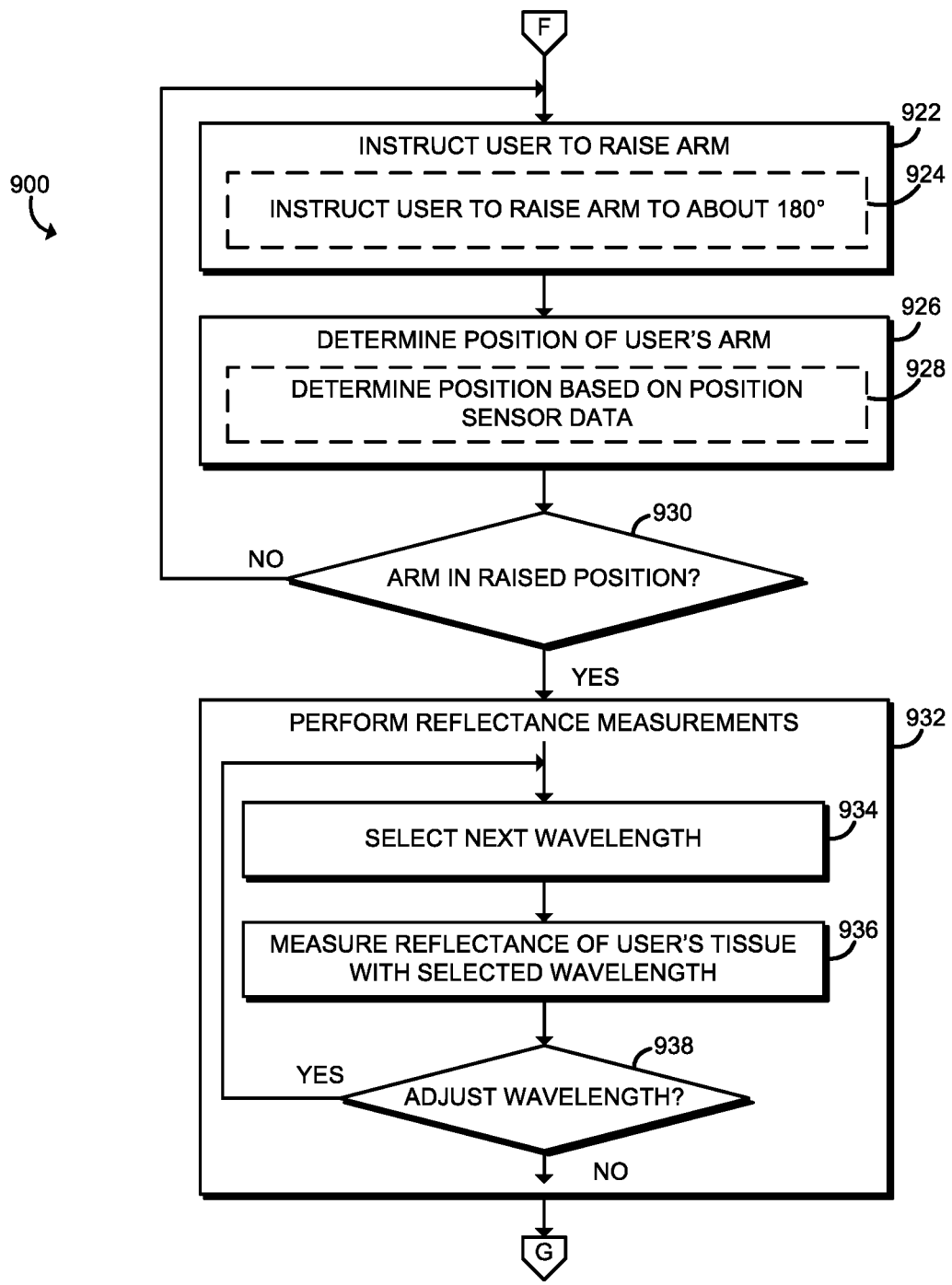
Figure 11:
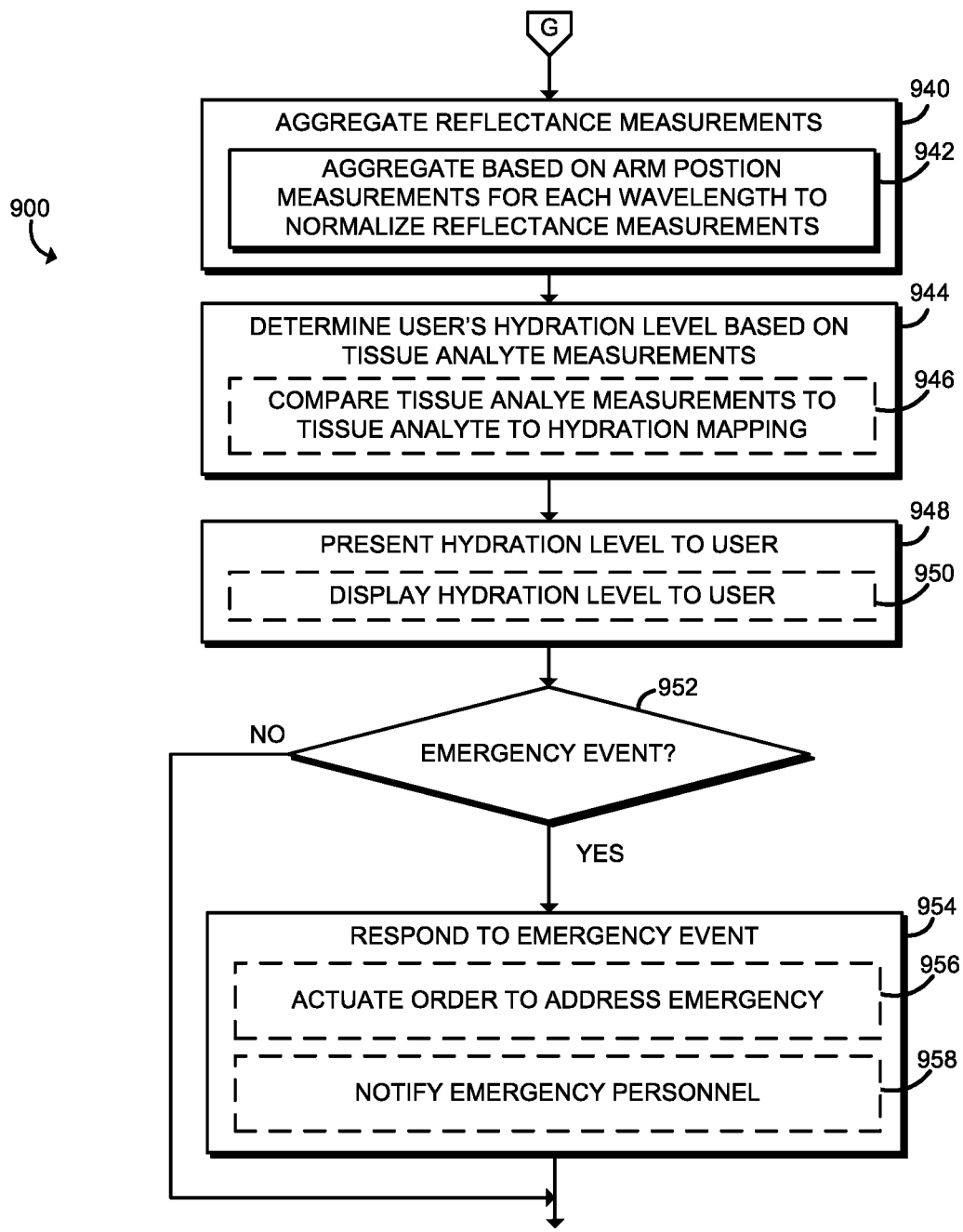

Referring now to FIGS. 9-11, the hydration measurement device 102 may execute a method 900 for measuring a hydration level of a user of the hydration measurement device 102 in some embodiments. Similarly to the method 300 of FIGS. 3-5, the method 900 of FIGS. 9-11 is usable to measure the hydration level of the user using a tissue analyte signal rather than, or in addition to, a user's blood analyte. The method 900 begins with block 902 in which the hydration measurement device 102 determines whether the user desires to determine his or her hydration level. To do so, in some embodiments, the hydration measurement device 102 may wait to receive an input from the user as described above. If it is determined that the user hydration is to be determined, the method 900 advances to block 904. However, if it is determined that user hydration is not to be determined, the method 900 loops back to the start of block 902.

In block 904, the hydration measurement device 102 instructs the user to position the user's arm in an initial "lower" position. For example, in block 906, the hydration measurement device 102 may instruct the user to lower his or her arm to about 0 degrees relative to the user's body (e.g., to instruct the user to place the user's arm by the user's side at approximately 0 degrees). It should be appreciated, however, that the "lower" position may be embodied as any position that is lower (e.g., has a smaller angle relative to the user's body) than the "raised" position and may have an angle relative to the user's body that is greater than 0 degrees in some embodiments. The hydration measurement device 102 may provide a visual, audible, or tactile instruction to the user.

In block 908, the hydration measurement device 102 determines the present position of the user's arm. In particular, the hydration measurement device 102 may determine the position of the user's arm to which the hydration measurement device 102 and/or the reflectance sensors 112 are attached. To do so, in some embodiments, in block 910, the hydration measurement device 102 may determine the position of the user's arm based on position sensor data from the arm position sensor(s) 114.

In block 912, the hydration measurement device 102 determines whether the arm is in the "lowered" position based on the analysis performed in block 908. If it is determined that the arm is not in a lowered position, the method 900 loops back to block 904 to attempt the process again. If it is determined that the arm is in a lowered position, the method 300 advances to block 314.

In block 914, the hydration measurement device 102 performs reflectance measurements. In order to perform the reflectance measurements, the hydration measurement device selects a next wavelength to be used for the reflectance measurements in block 916 (e.g., a wavelength selected from the range of 890 nm to 1600 nm). Subsequently, in block 918, the hydration measurement device 102 measures the reflectance of the user's tissue analyte with the selected wavelength. After performing the measurement, the hydration measurement device 102 determines in block 920 whether to adjust the wavelength based on previous measurements taken. For instance, if the hydration measurement device 102 already has a sufficient amount of reflectance measurements at various wavelengths, the method 900 advances to block 922 of FIG. 10, described below. However, if it is determined not enough reflectance measurements have been taken at different wavelengths, the method 900 loops back to block 916 to select another wavelength.

In block 922, shown in FIG. 10, the hydration measurement device 102 instructs the user to position the user's arm in a second "raised" position. For example, in block 924, the hydration measurement device 102 may instruct the user to raise his or her arm to about 180 degrees relative to the user's body (e.g., to instruct the user to position the user's arm above the user's shoulders at approximately 180 degrees). It should be appreciated, however, that the "raised" position may be embodied as any position that is raised or elevated (e.g., has a larger angle relative to the user's body) relative to the "lowered" position and may have an angle relative to the user's body that is less than 180 degrees in some embodiments. Again, the hydration measurement device 102 may provide a visual, audible, or tactile instruction to the user.

In block 926, the hydration measurement device 102 determines the position of the user's arm similarly to how the position of the arm is determined in block 908. Additionally, in some embodiments, in block 928, the hydration measurement device 102 may determine the position of the user's arm based on position sensor data from the arm position sensor(s) 114.

In block 930, the hydration measurement device 102 determines whether the arm is in the "raised" position based on the analysis performed in block 926. If it is determined that the arm is not in the "raised" position, the method loops back to block 922 to attempt the process again. After several attempts, the method 900 may restart back at block 904. If it is determined that the arm is in a raised position, the method 900 advances to block 932.

In block 932, the hydration measurement device 102 performs reflectance measurements similarly to block 914 of FIG. 9, described above. Block 934, block 936, and block 938 correspond to block 916, block 918, and block 920 of FIG. 9 and thus the descriptions of blocks 916, 918, 920 are applicable to the corresponding blocks 934, 936, 938. Subsequent to a determination that no further reflectance measurements are required, the method 900 advances to block 940 of FIG. 11, described below.

In block 940, shown in FIG. 11, the hydration measurement device 102 aggregates the reflectance measurements taken at the two different arm positions. To do so, in block 942 the hydration measurement device 102 aggregates the reflectance measurements taken at each position for each separate wavelength to normalize the reflectance measurements as described above.

In block 944, the hydration measurement device 102 determines the user's hydration level based on the tissue analyte measurements. To do so, in some embodiments, in block 946, the hydration measurement device 102 compares the tissue analyte measurements to a tissue analyte-to-hydration mapping. For example, the hydration measurement device 102 may match a tissue analyte value to the tissue analyte-to-hydration mapping in order to identify a hydration level.

After the hydration measurement device 102 determines the user's hydration level, the hydration measurement device 102 presents the hydration level to the user in block 948. To do so, in some embodiments, in block 950, the hydration measurement device 102 displays the hydration level to the user.

In block 952, the hydration measurement device 102 analyzes the determined hydration level from block 944 to determine whether there is an emergency event. For example, if the user is severely dehydrated it may be important that the user is at least notified and given assistance to recuperate. If it is determined there is no emergency event, the method 900 is completed. If there is an emergency event, the method 900 advances to block 954.

In block 954, the hydration measurement device 102 responds to the emergency event identified in block 952. To do so, in some embodiments, in block 956, the hydration measurement device 102 may actuate an order to address the emergency. For example, the hydration measurement device 102 may instruct the user not to exert himself or herself any further and to drink more liquids, such as water, in the event that the emergency event is severe user dehydration. Additionally or alternatively, in some embodiments, in block 958 the hydration measurement device 102 may notify emergency personnel of the emergency event. The emergency personnel may be authorities or other personnel that may assist the user to recuperate and get medical attention if required. After responding to the emergency event, the method 300 is completed.

Again, although the hydration measurement device 102 instructs the user to position the user's arm in the "raised" position followed by the "lowered" position in the illustrative method 900, it should be appreciated that the hydration measurement device 102 may instruct the user to position the user's arm in the "lowered" position first, followed by the "raised" position in other embodiments. Additionally, as discussed above, the hydration measurement device 102 may instruct the user to position the user's arm in an additional number of positions in other embodiments. Furthermore, the hydration measurement device 102 may perform method 600 but, similarly to method 900, measure a tissue analyte signal rather than or in addition to the user's blood analyte signal.

EXAMPLES

Illustrative examples of the technologies disclosed herein are provided below. An embodiment of the technologies may include any one or more, and any combination of, the examples described below.

Example 1 includes a hydration measurement device for measuring a hydration level of a user, the hydration measurement device comprising an arm position sensor to generate sensor data indicative of a position of an arm of the user; a reflectance sensor to perform reflectance measurements on the user; an arm position determiner to determine whether the arm of the user is in a plurality of positions based on the sensor data; a reflectance measurement manager to control the reflectance sensor to perform (i) a first reflectance measurement on the user to determine a first reflectance measurement value of the user's blood in response to a determination that the user's arm is in a first position and (ii) a second reflectance measurement on the user to determine a second reflectance measurement value of the user's blood in response to a determination that the user's arm is in a second position that is elevated relative to the first position; and a hydration determiner to determine (i) a hematocrit of the user's blood based on the first reflectance measurement value and second reflectance measurement value and (ii) the hydration level of the user based on the determined hematocrit.

Example 2 includes the subject matter of Example 1, and wherein the first position is an arm position at which the arm of the user is at an angle of about 0 degrees relative to a body of the user and the second position is an arm position at which the arm of the user is at an angle of about 180 degrees relative to the body of the user.

Example 3 includes the subject matter of any of Examples 1 and 2, and further including an output device to present (i) a first instruction to the user to position the arm of the user in the first position prior to performance of the first reflectance measurement and (ii) a second instruction to the user to position the arm of the user into the second position prior to performance of the second reflectance measurement.

Example 4 includes the subject matter of any of Examples 1-3, and wherein each of the first and second instructions is at least one of a visual, audible, or tactile instruction to the user.

Example 5 includes the subject matter of any of Examples 1-4, and wherein to perform the first reflectance measurement on the user comprises to perform a plurality of first optical reflectance measurements on the user, wherein each first optical reflectance measurement of the plurality of first optical reflectance measurements use a different wavelength of light.

Example 6 includes the subject matter of any of Examples 1-5, and wherein to perform the second reflectance measurement on the user comprises to perform a plurality of second optical reflectance measurements on the user, wherein each second optical reflectance measurement of the plurality of second optical reflectance measurements use a different wavelength of light, wherein each wavelength of the second optical reflectance measurements match a corresponding wavelength of the first optical reflectance measurements.

Example 7 includes the subject matter of any of Examples 1-6, and wherein the hydration determiner is further to aggregate the first optical reflectance measurement and the second optical reflectance measurement to normalize the corresponding first optical reflectance measurement.

Example 8 includes the subject matter of any of Examples 1-7, and wherein the hydration determiner is further to determine a normalized reflectance measurement value, wherein to determine the normalized reflectance measurement value comprises to normalize the first reflectance measurement value based on the second reflectance measurement value.

Example 9 includes the subject matter of any of Examples 1-8, and wherein to determine the hematocrit of the user's blood comprises to determine the hematocrit of the user's blood based on the normalized reflectance measurement value.

Example 10 includes the subject matter of any of Examples 1-9, and wherein to normalize the first reflectance measurement value comprises to adjust the first reflectance measurement value based on the second reflectance measurement value.

Example 11 includes the subject matter of any of Examples 1-10, and wherein to determine the hydration level of the user comprises to compare the determined hematocrit to a hematocrit-to-hydration mapping maintained by the hydration measurement device.

Example 12 includes the subject matter of any of Examples 1-11, and further including an output device to present the determined hydration level to the user.

Example 13 includes the subject matter of any of Examples 1-12, and further including an output controller to (i) determine whether the user requires emergency attention based on the determined hydration level of the user and (ii) communicate with a remote compute device to alert emergency personnel in response to a determination the user requires emergency attention.

Example 14 includes the subject matter of any of Examples 1-13, and wherein the arm position determiner is to determine whether the arm is in the first position prior to a determination of whether the arm is in the second position.

Example 15 includes the subject matter of any of Examples 1-14, and wherein the arm position determiner is to determine whether the arm is in the second position prior to a determination of whether the arm is in the first position.

Example 16 includes the subject matter of any of Examples 1-15, and wherein the hydration determiner is further to determine whether a temporal length between the performance of the first reflectance measurement and the performance of the second reflectance measurement is in compliance with a reference relationship with a maximum temporal length threshold, wherein to determine the hematocrit of the user comprises to determine the hematocrit of the user based on the first reflectance measurement value and second reflectance measurement value in response to a determination that the temporal length is in compliance with the reference relationship with the maximum temporal length threshold.

Example 17 includes a method for measuring a hydration level of a user, the method comprising determining, by a hydration measurement device worn by the user, whether an arm of the user is in a first position; performing, by the hydration measurement device and in response to a determination that the user's arm is in the first position, a first reflectance measurement on the user to determine a first reflectance measurement value of the user's blood; determining, by the hydration measurement device, whether the arm of the user is in a second position that is elevated relative to the first position; performing, by the hydration measurement device and in response to a determination that the user's arm is in the second position, a second reflectance measurement on the user to determine a second reflectance measurement value of the user's blood; determining, by the hydration measurement device, a hematocrit of the user's blood based on the first reflectance measurement value and second reflectance measurement value; and determining, by the hydration measurement device, the hydration level of the user based on the determined hematocrit.

Example 18 includes the subject matter of Example 17, and wherein determining whether the arm of the user is in the first position comprises receiving sensor data from an arm position sensor of the hydration measurement device, wherein the sensor data is indicative of a present position of the arm of the user; and determining, based on the sensor data, whether the arm of the user is in the first position.

Example 19 includes the subject matter of any of Examples 17 and 18, and wherein determining whether the arm of the user is in the second position comprises receiving additional sensor data from the arm position sensor of the hydration measurement device; and determining, based on the sensor data, whether the arm of the user is in the second position.

Example 20 includes the subject matter of any of Examples 17-19, and wherein the first position is an arm position at which the arm of the user is at an angle of about 0 degrees relative to a body of the user and the second position is an arm position at which the arm of the user is at an angle of about 180 degrees relative to the body of the user.

Example 21 includes the subject matter of any of Examples 17-20, and further including presenting, by the hydration measurement device, a first instruction to the user to position the arm of the user into the first position prior to performing the first reflectance measurement; and presenting, by the hydration measurement device, a second instruction to the user to position the arm of the user into the second position prior to performing the second reflectance measurement.

Example 22 includes the subject matter of any of Examples 17-21, and wherein each of the first and second instructions is at least one of a visual, audible, or tactile instruction to the user.

Example 23 includes the subject matter of any of Examples 17-22, and wherein performing the first reflectance measurement on the user comprises performing a plurality of first optical reflectance measurements on the user, wherein each first optical reflectance measurement of the plurality of first optical reflectance measurements uses a different wavelength of light.

Example 24 includes the subject matter of any of Examples 17-23, and wherein performing the second reflectance measurement on the user comprises performing a plurality of second optical reflectance measurements on the user, wherein each second optical reflectance measurement of the plurality of second optical reflectance measurements uses a different wavelength of light, wherein each wavelength of the second optical reflectance measurements matches a corresponding wavelength of the first optical reflectance measurements.

Example 25 includes the subject matter of any of Examples 17-24, and further including aggregating, by the hydration measurement device and for each wavelength, the first optical reflectance measurement and the second optical reflectance measurement to normalize the corresponding first optical reflectance measurement.

Example 26 includes the subject matter of any of Examples 17-25, and further including determining a normalized reflectance measurement value by normalizing the first reflectance measurement value based on the second reflectance measurement value.

Example 27 includes the subject matter of any of Examples 17-26, and wherein determining the hematocrit of the user's blood comprises determining the hematocrit of the user's blood based on the normalized reflectance measurement value.

Example 28 includes the subject matter of any of Examples 17-27, and wherein normalizing the first reflectance measurement value comprises adjusting the first reflectance measurement value based on the second reflectance measurement value.

Example 29 includes the subject matter of any of Examples 17-28, and wherein determining the hydration level of the user comprises comparing the determined hematocrit to a hematocrit-to-hydration mapping maintained by the hydration measurement device.

Example 30 includes the subject matter of any of Examples 17-29, and further including presenting the determined hydration level to the user.

Example 31 includes the subject matter of any of Examples 17-30, and further including determining, by the hydration measurement device, whether the user requires emergency attention based on the determined hydration level of the user; and communicating with a remote compute device to alert emergency personnel in response to determining the user requires emergency attention.

Example 32 includes the subject matter of any of Examples 17-31, and wherein determining whether the arm of the user is in the second position occurs prior to determining whether the arm of the user is in the first position.

Example 33 includes the subject matter of any of Examples 17-32, and further including determining, by the hydration measurement device, whether a temporal length between the performing of the first reflectance measurement and the performing of the second reflectance measurement satisfies a reference relationship with a maximum temporal length threshold, wherein determining the hematocrit of the user comprises determining the hematocrit of the user based on the first reflectance measurement value and second reflectance measurement value in response to a determination that the temporal length satisfies the reference relationship with the maximum temporal length threshold.

Example 34 includes one or more computer-readable storage media comprising a plurality of instructions that, when executed by a hydration measurement device, cause the hydration measurement device to perform the method of any of Examples 17-33.

Example 35 includes a hydration measurement device comprising means for determining whether an arm of the user is in a first position; means for performing, in response to a determination that the user's arm is in the first position, a first reflectance measurement on the user to determine a first reflectance measurement value of the user's blood; means for determining whether the arm of the user is in a second position that is elevated relative to the first position; means for performing, in response to a determination that the user's arm is in the second position, a second reflectance measurement on the user to determine a second reflectance measurement value of the user's blood; means for determining a hematocrit of the user's blood based on the first reflectance measurement value and second reflectance measurement value; and means for determining the hydration level of the user based on the determined hematocrit.

Example 36 includes the subject matter of Example 35, and wherein the means for determining whether the arm of the user is in the first position comprises means for receiving sensor data from an arm position sensor of the hydration measurement device, wherein the sensor data is indicative of a present position of the arm of the user; and means for determining, based on the sensor data, whether the arm of the user is in the first position.

Example 37 includes the subject matter of any of Examples 35 and 36, and wherein the means for determining whether the arm of the user is in the second position comprises means for receiving additional sensor data from the arm position sensor of the hydration measurement device; and means for determining, based on the sensor data, whether the arm of the user is in the second position.

Example 38 includes the subject matter of any of Examples 35-37, and wherein the first position is an arm position at which the arm of the user is at an angle of about 0 degrees relative to a body of the user and the second position is an arm position at which the arm of the user is at an angle of about 180 degrees relative to the body of the user.

Example 39 includes the subject matter of any of Examples 35-38, and further including means for presenting a first instruction to the user to position the arm of the user into the first position prior to performing the first reflectance measurement; and means for presenting a second instruction to the user to position the arm of the user into the second position prior to performing the second reflectance measurement.

Example 40 includes the subject matter of any of Examples 35-39, and wherein each of the first and second instructions is at least one of a visual, audible, or tactile instruction to the user.

Example 41 includes the subject matter of any of Examples 35-40, and wherein the means for performing the first reflectance measurement on the user comprises means for performing a plurality of first optical reflectance measurements on the user, wherein each first optical reflectance measurement of the plurality of first optical reflectance measurements uses a different wavelength of light.

Example 42 includes the subject matter of any of Examples 35-41, and wherein the means for performing the second reflectance measurement on the user comprises means for performing a plurality of second optical reflectance measurements on the user, wherein each second optical reflectance measurement of the plurality of second optical reflectance measurements uses a different wavelength of light, wherein each wavelength of the second optical reflectance measurements matches a corresponding wavelength of the first optical reflectance measurements.

Example 43 includes the subject matter of any of Examples 35-42, and further including means for aggregating, for each wavelength, the first optical reflectance measurement and the second optical reflectance measurement to normalize the corresponding first optical reflectance measurement.

Example 44 includes the subject matter of any of Examples 35-43, and further including means for determining a normalized reflectance measurement value by normalizing the first reflectance measurement value based on the second reflectance measurement value.

Example 45 includes the subject matter of any of Examples 35-44, and wherein the means for determining the hematocrit of the user's blood comprises means for determining the hematocrit of the user's blood based on the normalized reflectance measurement value.

Example 46 includes the subject matter of any of Examples 35-45, and wherein the means for normalizing the first reflectance measurement value comprises means for adjusting the first reflectance measurement value based on the second reflectance measurement value.

Example 47 includes the subject matter of any of Examples 35-46, and wherein the means for determining the hydration level of the user comprises means for comparing the determined hematocrit to a hematocrit-to-hydration mapping maintained by the hydration measurement device.

Example 48 includes the subject matter of any of Examples 35-47, and further including means for presenting the determined hydration level to the user.

Example 49 includes the subject matter of any of Examples 35-48, and further including means for determining whether the user requires emergency attention based on the determined hydration level of the user; and means for communicating with a remote compute device to alert emergency personnel in response to determining the user requires emergency attention.

Example 50 includes the subject matter of any of Examples 35-49, and wherein the means for determining whether the arm of the user is in the second position occurs prior to determining whether the arm of the user is in the first position.

Example 51 includes the subject matter of any of Examples 35-50, and further including means for determining whether a temporal length between the performing of the first reflectance measurement and the performing of the second reflectance measurement satisfies a reference relationship with a maximum temporal length threshold, wherein the means for determining the hematocrit of the user comprises means for determining the hematocrit of the user based on the first reflectance measurement value and second reflectance measurement value in response to a determination that the temporal length satisfies the reference relationship with the maximum temporal length threshold.

Example 52 includes a hydration measurement device for measuring a hydration level of a user, the hydration measurement device comprising an arm position sensor to generate sensor data indicative of a position of an arm of the user; a reflectance sensor to perform reflectance measurements on the user; an arm position determiner to determine (i) whether the arm of the user is in a first position based on the sensor data and (ii) whether the arm of the user is in a second position that is elevated relative to the first position based on the sensor data; a reflectance measurement manager to control the reflectance sensor to perform (i) a first reflectance measurement on the user to determine a first reflectance measurement value of the user's tissue in response to a determination that the user's arm is in the first position and (ii) a second reflectance measurement on the user to determine a second reflectance measurement value of the user's tissue in response to a determination that the user's arm is in the second position; and a hydration determiner to determine (i) a tissue analyte measurement value based on the first reflectance measurement value and second reflectance measurement value and (ii) the hydration level of the user based on the tissue analyte measurement value.

Example 53 includes the subject matter of Example 52, and wherein the first position is an arm position at which the arm of the user is at an angle of about 0 degrees relative to a body of the user and the second position is an arm position at which the arm of the user is at an angle of about 180 degrees relative to the body of the user.

Example 54 includes the subject matter of any of Examples 52 and 53, and further including an output device to present (i) a first instruction to the user to position the arm of the user in the first position prior to performance of the first reflectance measurement and (ii) a second instruction to the user to position the arm of the user into the second position prior to performance of the second reflectance measurement.

Example 55 includes the subject matter of any of Examples 52-54, and wherein each of the first and second instructions is at least one of a visual, audible, or tactile instruction to the user.

Example 56 includes the subject matter of any of Examples 52-55, and wherein to perform the first reflectance measurement on the user comprises to perform a plurality of first optical reflectance measurements on the user, wherein each first optical reflectance measurement of the plurality of first optical reflectance measurements use a different wavelength of light.

Example 57 includes the subject matter of any of Examples 52-56, and wherein to perform the second reflectance measurement on the user comprises to perform a plurality of second optical reflectance measurements on the user, wherein each second optical reflectance measurement of the plurality of second optical reflectance measurements use a different wavelength of light, wherein each wavelength of the second optical reflectance measurements match a corresponding wavelength of the first optical reflectance measurements.

Example 58 includes the subject matter of any of Examples 52-57, and wherein the hydration determiner is further to aggregate the first optical reflectance measurement and the second optical reflectance measurement to normalize the corresponding first optical reflectance measurement.

Example 59 includes the subject matter of any of Examples 52-58, and wherein the hydration determiner is further to determine a normalized reflectance measurement value, wherein to determine the normalized reflectance measurement value comprises to normalize the first reflectance measurement value based on the second reflectance measurement value.

Example 60 includes the subject matter of any of Examples 52-59, and wherein to determine the tissue analyte measurement value of the user's tissue comprises to determine the tissue analyte measurement value of the user's tissue based on the normalized reflectance measurement value.

Example 61 includes the subject matter of any of Examples 52-60, and wherein to normalize the first reflectance measurement value comprises to adjust the first reflectance measurement value based on the second reflectance measurement value.

Example 62 includes the subject matter of any of Examples 52-61, and wherein to determine the hydration level of the user comprises to compare the tissue analyte measurement value to a tissue analyte-to-hydration mapping maintained by the hydration measurement device.

Example 63 includes the subject matter of any of Examples 52-62, and further including an output device to present the determined hydration level to the user.

Example 64 includes the subject matter of any of Examples 52-63, and further including an output controller to (i) determine whether the user requires emergency attention based on the determined hydration level of the user and (ii) communicate with a remote compute device to alert emergency personnel in response to a determination the user requires emergency attention.

Example 65 includes the subject matter of any of Examples 52-64, and wherein the arm position determiner is further to determine whether the arm is in the first position prior to a determination of whether the arm is in the second position.

Example 66 includes the subject matter of any of Examples 52-65, and wherein the arm position determiner is further to determine whether the arm is in the second position prior to a determination of whether the arm is in the first position.

Example 67 includes the subject matter of any of Examples 52-66, and wherein the hydration determiner is further to determine whether a temporal length between the performance of the first reflectance measurement and the performance of the second reflectance measurement is in compliance with a reference relationship with a maximum temporal length threshold, wherein to determine the tissue analyte measurement value of the user comprises to determine the tissue analyte measurement value of the user based on the first reflectance measurement value and second reflectance measurement value in response to a determination that the temporal length is in compliance with the reference relationship with the maximum temporal length threshold.

The invention claimed is:

1. A hydration measurement device for measuring a hydration level of a user, the hydration measurement device comprising:
an arm position sensor to generate sensor data indicative of a position of an arm of the user;
a reflectance sensor to perform reflectance measurements on the user;
an arm position determiner to determine whether the arm of the user is in a plurality of positions based on the sensor data;
a reflectance measurement manager to control the reflectance sensor to perform (i) a first reflectance measurement on the user to determine a first reflectance measurement value of the user's blood in response to a determination that the user's arm is in a first position and (ii) a second reflectance measurement on the user to determine a second reflectance measurement value of the user's blood in response to a determination that the user's arm is in a second position that is elevated relative to the first position; and
a hydration determiner to determine (i) a hematocrit of the user's blood based on the first reflectance measurement value and second reflectance measurement value and (ii) the hydration level of the user based on the determined hematocrit.

2. The hydration measurement device of claim 1, wherein the first position is an arm position at which the arm of the user is at an angle of about 0 degrees relative to a body of the user and the second position is an arm position at which the arm of the user is at an angle of about 180 degrees relative to the body of the user.

3. The hydration measurement device of claim 1, further comprising an output device to present (i) a first instruction to the user to position the arm of the user in the first position prior to performance of the first reflectance measurement and (ii) a second instruction to the user to position the arm of the user into the second position prior to performance of the second reflectance measurement.

4. The hydration measurement device of claim 1, wherein to perform the first reflectance measurement on the user comprises to perform a plurality of first optical reflectance measurements on the user, wherein each first optical reflectance measurement of the plurality of first optical reflectance measurements use a different wavelength of light.

5. The hydration measurement device of claim 4, wherein to perform the second reflectance measurement on the user comprises to perform a plurality of second optical reflectance measurements on the user, wherein each second optical reflectance measurement of the plurality of second optical reflectance measurements use a different wavelength of light, wherein each wavelength of the second optical reflectance measurements match a corresponding wavelength of the first optical reflectance measurements, and
wherein the hydration determiner is further to aggregate the first optical reflectance measurement and the second optical reflectance measurement to normalize the corresponding first optical reflectance measurement.

6. The hydration measurement device of claim 1, wherein the hydration determiner is further to determine a normalized reflectance measurement value, wherein to determine the normalized reflectance measurement value comprises to normalize the first reflectance measurement value based on the second reflectance measurement value.

7. The hydration measurement device of claim 6, wherein to determine the hematocrit of the user's blood comprises to determine the hematocrit of the user's blood based on the normalized reflectance measurement value.

8. The hydration measurement device of claim 1, wherein to determine the hydration level of the user comprises to compare the determined hematocrit to a hematocrit-to-hydration mapping maintained by the hydration measurement device.

9. The hydration measurement device of claim 1, wherein the hydration determiner is further to determine whether a temporal length between the performance of the first reflectance measurement and the performance of the second reflectance measurement is in compliance with a reference relationship with a maximum temporal length threshold,
wherein to determine the hematocrit of the user comprises to determine the hematocrit of the user based on the first reflectance measurement value and second reflectance measurement value in response to a determination that the temporal length is in compliance with the reference relationship with the maximum temporal length threshold.

10. One or more computer-readable storage media comprising a plurality of instructions that, when executed by a hydration measurement device, cause the hydration measurement device to:
determine whether an arm of the user is in a first position;
perform, in response to a determination that the user's arm is in the first position, a first reflectance measurement on the user to determine a first reflectance measurement value of the user's blood;
determine whether the arm of the user is in a second position that is elevated relative to the first position;
perform, in response to a determination that the user's arm is in the second position, a second reflectance measurement on the user to determine a second reflectance measurement value of the user's blood;
determine a hematocrit of the user's blood based on the first reflectance measurement value and second reflectance measurement value; and
determine the hydration level of the user based on the determined hematocrit.

11. The one or more computer-readable storage media of claim 10, wherein to determine whether the arm of the user is in the first position comprises to:
receive sensor data from an arm position sensor of the hydration measurement device, wherein the sensor data is indicative of a present position of the arm of the user; and
determine, based on the sensor data, whether the arm of the user is in the first position.

12. The one or more computer-readable storage media of claim 11, wherein to determine whether the arm of the user is in the second position comprises to:
receive additional sensor data from the arm position sensor of the hydration measurement device; and
determine, based on the sensor data, whether the arm of the user is in the second position.

13. The one or more computer-readable storage media of claim 12, wherein to perform the first reflectance measurement on the user comprises to perform a plurality of first optical reflectance measurements on the user, wherein each first optical reflectance measurement of the plurality of first optical reflectance measurements uses a different wavelength of light.

14. The one or more computer-readable storage media of claim 13, wherein to perform the second reflectance measurement on the user comprises to perform a plurality of second optical reflectance measurements on the user, wherein each second optical reflectance measurement of the plurality of second optical reflectance measurements uses a different wavelength of light, wherein each wavelength of the second optical reflectance measurements matches a corresponding wavelength of the first optical reflectance measurements, and wherein the plurality of instructions, when executed, further cause the hydration measurement device to aggregate, for each wavelength, the first optical reflectance measurement and the second optical reflectance measurement to normalize the corresponding first optical reflectance measurement.

15. The one or more computer-readable storage media of claim 10, wherein the plurality of instructions, when executed, further cause the hydration measurement device to determine a normalized reflectance measurement value by normalizing the first reflectance measurement value based on the second reflectance measurement value.

16. The one or more computer-readable storage media of claim 15, wherein to determine the hematocrit of the user's blood comprises to determine the hematocrit of the user's blood based on the normalized reflectance measurement value.

17. The one or more computer-readable storage media of claim 10, wherein the plurality of instructions, when executed, further cause the hydration measurement device to:

determine whether a temporal length between the performing of the first reflectance measurement and the performing of the second reflectance measurement satisfies a reference relationship with a maximum temporal length threshold, wherein to determine the hematocrit of the user comprises to determine the hematocrit of the user based on the first reflectance measurement value and second reflectance measurement value in response to a determination that the temporal length satisfies the reference relationship with the maximum temporal length threshold.

18. A method for measuring a hydration level of a user, the method comprising:

determining, by a hydration measurement device worn by the user, whether an arm of the user is in a first position;

performing, by the hydration measurement device and in response to a determination that the user's arm is in the first position, a first reflectance measurement on the user to determine a first reflectance measurement value of the user's blood;

determining, by the hydration measurement device, whether the arm of the user is in a second position that is elevated relative to the first position;

performing, by the hydration measurement device and in response to a determination that the user's arm is in the second position, a second reflectance measurement on the user to determine a second reflectance measurement value of the user's blood;

determining, by the hydration measurement device, a hematocrit of the user's blood based on the first reflectance measurement value and second reflectance measurement value; and determining, by the hydration measurement device, the hydration level of the user based on the determined hematocrit.

19. The method of claim 18, wherein determining whether the arm of the user is in the first position comprises:

receiving sensor data from an arm position sensor of the hydration measurement device, wherein the sensor data is indicative of a present position of the arm of the user; and determining, based on the sensor data, whether the arm of the user is in the first position.

20. The method of claim 19, wherein determining whether the arm of the user is in the second position comprises:

receiving additional sensor data from the arm position sensor of the hydration measurement device; and determining, based on the sensor data, whether the arm of the user is in the second position.

21. The method of claim 18, wherein performing the first reflectance measurement on the user comprises performing a plurality of first optical reflectance measurements on the user, wherein each first optical reflectance measurement of the plurality of first optical reflectance measurements uses a different wavelength of light.

22. The method of claim 21, wherein performing the second reflectance measurement on the user comprises performing a plurality of second optical reflectance measurements on the user, wherein each second optical reflectance measurement of the plurality of second optical reflectance measurements uses a different wavelength of light, wherein each wavelength of the second optical reflectance measurements matches a corresponding wavelength of the first optical reflectance measurements, and further comprising aggregating, by the hydration measurement device and for each wavelength, the first optical reflectance measurement and the second optical reflectance measurement to normalize the corresponding first optical reflectance measurement.

23. The method of claim 18, further comprising determining a normalized reflectance measurement value by normalizing the first reflectance measurement value based on the second reflectance measurement value.

24. The method of claim 23, wherein determining the hematocrit of the user's blood comprises determining the hematocrit of the user's blood based on the normalized reflectance measurement value.

25. The method of claim 18, further comprising:

determining, by the hydration measurement device, whether a temporal length between the performing of the first reflectance measurement and the performing of the second reflectance measurement satisfies a reference relationship with a maximum temporal length threshold, wherein determining the hematocrit of the user comprises determining the hematocrit of the user based on the first reflectance measurement value and second reflectance measurement value in response to a determination that the temporal length satisfies the reference relationship with the maximum temporal length threshold.

\* \* \* \* \*